(12) United States Patent
Rouse et al.

(10) Patent No.: US 12,076,517 B2
(45) Date of Patent: Sep. 3, 2024

(54) COMPUTERIZED ORAL PRESCRIPTION ADMINISTRATION DEVICES AND ASSOCIATED SYSTEMS AND METHODS

(71) Applicant: BERKSHIRE BIOMEDICAL, LLC, Dallas, TX (US)

(72) Inventors: Thomas M. Rouse, Dallas, TX (US); Susan B. Owen, Dallas, TX (US); Christy Corey, Fishers, IN (US)

(73) Assignee: Berkshire Biomedical Corporation, Dallas, TX (US)

( * ) Notice: Subject to any disclaimer, the term of this patent is extended or adjusted under 35 U.S.C. 154(b) by 53 days.

(21) Appl. No.: 17/379,262

(22) Filed: Jul. 19, 2021

(65) Prior Publication Data

US 2021/0346660 A1 Nov. 11, 2021

Related U.S. Application Data

(63) Continuation of application No. 16/246,122, filed on Jan. 11, 2019, now Pat. No. 11,097,085, which is a
(Continued)

(51) Int. Cl.
*A61M 31/00* (2006.01)
*G16H 20/13* (2018.01)
(Continued)

(52) U.S. Cl.
CPC ............ *A61M 31/00* (2013.01); *G16H 20/13* (2018.01); *G16H 20/17* (2018.01); *G16H 40/67* (2018.01);
(Continued)

(58) Field of Classification Search
CPC ....... A61C 19/063; A61C 7/08; A61C 19/066; A61C 17/024; A61C 17/028;
(Continued)

(56) References Cited

U.S. PATENT DOCUMENTS

| | | | |
|---|---|---|---|
| 3,840,992 A | 10/1974 | English | |
| 4,116,195 A | 9/1978 | James | |

(Continued)

FOREIGN PATENT DOCUMENTS

| | | | | |
|---|---|---|---|---|
| CA | 2906116 A1 | * | 9/2014 | ........... A61B 5/0022 |
| CN | 1997421 | | 7/2007 | |

(Continued)

OTHER PUBLICATIONS

Japanese Office Action, Decision of Final Rejection, Application No. 2019-558990, Mar. 31, 2022, with Translation, 5 pages.
(Continued)

*Primary Examiner* — Joseph D Burgess
(74) *Attorney, Agent, or Firm* — Haynes and Boone, LLP

(57) ABSTRACT

Computerized oral prescription administration (COPA) devices, systems, and methods are provided. In one embodiment, a method of managing substance administration is provided. The method comprises receiving, by a substance management system, a dosage instruction for administering a substance to an intended user through a mouthpiece including a recess sized and shaped to receive a unique dentition of the intended user; receiving, by the substance management system, activity information associated with administering the substance to the intended user; and generating, by the substance management system, a record based on the received activity information.

19 Claims, 9 Drawing Sheets

Related U.S. Application Data continuation of application No. 15/674,046, filed on Aug. 10, 2017, now Pat. No. 10,188,840, which is a continuation of application No. 15/406,043, filed on Jan. 13, 2017, now Pat. No. 9,731,103.

(51) Int. Cl.
  *G16H 20/17* (2018.01)
  *G16H 40/67* (2018.01)

(52) U.S. Cl.
  CPC ... *A61M 2205/13* (2013.01); *A61M 2205/332* (2013.01); *A61M 2205/3523* (2013.01); *A61M 2205/3553* (2013.01); *A61M 2205/52* (2013.01); *A61M 2205/587* (2013.01); *A61M 2205/609* (2013.01); *A61M 2209/086* (2013.01)

(58) Field of Classification Search
  CPC ........ A61M 2210/0637; A61M 31/002; A61M 2209/086; A61M 5/14244; A61M 2210/0625; A61M 16/049; A61M 2005/14513; A61M 5/14236; A61M 11/00; G16H 40/67; G16H 40/63; A61B 5/682; A61K 9/0004; A61K 9/0053; A61J 7/0092; A61J 7/0076; A61N 1/0448
  See application file for complete search history.

(56) References Cited

U.S. PATENT DOCUMENTS

| | | |
|---|---|---|
| 4,237,884 A | 12/1980 | Erickson et al. |
| 4,353,365 A | 10/1982 | Hallworth et al. |
| 4,428,502 A | 1/1984 | Veltri |
| 4,474,308 A | 10/1984 | Bergeron |
| 4,717,042 A | 1/1988 | McLaughlin |
| 4,784,288 A | 11/1988 | Jennings |
| 5,159,581 A | 10/1992 | Agans |
| 5,583,831 A | 12/1996 | Churchill et al. |
| 5,791,515 A | 8/1998 | Khan et al. |
| 5,852,590 A | 12/1998 | de la Huerga |
| H1782 H | 2/1999 | Wicks et al. |
| 5,881,721 A | 3/1999 | Bunce et al. |
| 5,947,329 A | 9/1999 | Bailey |
| 5,960,085 A | 9/1999 | de la Huerga |
| 5,971,594 A | 10/1999 | Sahai et al. |
| 5,990,782 A | 11/1999 | Lee |
| 6,018,289 A | 1/2000 | Sekura et al. |
| 6,032,155 A | 2/2000 | de la Huerga |
| 6,082,363 A | 7/2000 | Washburn |
| 6,089,864 A | 7/2000 | Buckner et al. |
| 6,112,942 A | 9/2000 | Deacon |
| 6,119,684 A | 9/2000 | Nohl et al. |
| 6,145,697 A | 11/2000 | Gudish |
| 6,163,736 A | 12/2000 | Halfacre |
| 6,198,383 B1 | 3/2001 | Sekura et al. |
| 6,259,654 B1 | 7/2001 | de la Huerga |
| 6,304,797 B1 | 10/2001 | Shusterman |
| 6,332,100 B1 | 12/2001 | Sahai et al. |
| 6,335,907 B1 | 1/2002 | Momich et al. |
| 6,408,330 B1 | 6/2002 | DeLaHuerga |
| 6,431,399 B2 | 8/2002 | Gabel et al. |
| 6,529,446 B1 | 3/2003 | de la Huerga |
| 6,604,650 B2 | 8/2003 | Sagar |
| 6,611,733 B1 | 8/2003 | De La Huerga |
| 6,702,146 B2 | 3/2004 | Varis |
| 6,779,024 B2 | 8/2004 | DeLaHuerga |
| 6,834,775 B1 | 12/2004 | Collins |
| 6,958,691 B1 | 10/2005 | Anderson et al. |
| 6,988,634 B2 | 1/2006 | Varis |
| 7,006,894 B2 | 2/2006 | de la Huerga |
| 7,042,807 B1 | 5/2006 | Breen |
| 7,048,141 B2 | 5/2006 | Abdulhay et al. |
| 7,061,831 B2 | 6/2006 | De La Huerga |
| 7,072,738 B2 | 7/2006 | Bonney et al. |
| 7,073,685 B1 | 7/2006 | Giraud et al. |
| 7,100,797 B2 | 9/2006 | Kahn et al. |
| 7,104,417 B2 | 9/2006 | Hilliard |
| 7,128,240 B1 | 10/2006 | Oesch |
| 7,147,127 B2 | 12/2006 | Lepke et al. |
| 7,178,688 B2 | 2/2007 | Naufel et al. |
| 7,182,955 B2 | 2/2007 | Hart et al. |
| 7,213,721 B2 | 5/2007 | Abdulhay et al. |
| 7,216,802 B1 | 5/2007 | De La Huerga |
| 7,269,476 B2 | 9/2007 | Ratnakar |
| 7,295,890 B2 | 11/2007 | Jean-Pierre |
| 7,302,311 B2 | 11/2007 | Varis |
| 7,328,859 B2 | 2/2008 | Hornsby et al. |
| 7,359,765 B2 | 4/2008 | Varvarelis et al. |
| 7,366,675 B1 | 4/2008 | Walker et al. |
| 7,392,918 B2 | 7/2008 | Holloway et al. |
| 7,404,500 B2 | 7/2008 | Marteau et al. |
| 7,648,093 B2 | 1/2010 | Kroger |
| 7,711,449 B2 | 5/2010 | Abdulhay et al. |
| 7,715,277 B2 | 5/2010 | de la Huerga |
| 7,719,927 B1 | 5/2010 | Robinson et al. |
| 7,801,745 B2 | 9/2010 | Walker et al. |
| 7,810,673 B2 | 10/2010 | Lancesseur et al. |
| 7,831,336 B2 | 11/2010 | Gumpert |
| 7,844,361 B2 | 11/2010 | Jean-Pierre |
| 7,885,725 B2 | 2/2011 | Dunn |
| 7,941,534 B2 | 5/2011 | de la Huerga |
| 7,978,564 B2 | 7/2011 | De La Huerga |
| 7,988,016 B2 | 8/2011 | Klein et al. |
| 7,996,106 B2 | 8/2011 | Ervin |
| 8,019,471 B2 | 9/2011 | Bogash et al. |
| 8,028,856 B2 | 10/2011 | Erdelyi et al. |
| 8,029,538 B2 | 10/2011 | Burroughs et al. |
| 8,033,422 B2 | 10/2011 | Estrada |
| 8,055,509 B1 | 11/2011 | Walker et al. |
| 8,062,248 B2 | 11/2011 | Kindel |
| 8,069,056 B2 | 11/2011 | Walker et al. |
| 8,135,497 B2 | 3/2012 | Joslyn |
| 8,195,330 B2 | 6/2012 | Coe |
| 8,212,677 B2 | 7/2012 | Ferguson |
| 8,226,978 B2 | 7/2012 | Palmer et al. |
| 8,269,613 B2 | 9/2012 | Lazar |
| 8,279,076 B2 | 10/2012 | Johnson |
| 8,284,068 B2 | 10/2012 | Johnson |
| 8,319,613 B2 | 11/2012 | Lazar |
| 8,326,455 B2 | 12/2012 | Dunn |
| 8,357,114 B2 | 1/2013 | Poutiatine et al. |
| 8,391,104 B2 | 3/2013 | de la Huerga |
| 8,392,020 B2 | 3/2013 | Terzini |
| 8,417,378 B2 | 4/2013 | Joslyn |
| 8,483,872 B2 | 7/2013 | Ratnakar |
| 8,499,966 B2 | 8/2013 | Palmer et al. |
| 8,502,671 B2 | 8/2013 | Marcovici |
| 8,502,692 B2 | 8/2013 | Johnson |
| 8,511,478 B2 | 8/2013 | Terzini |
| 8,548,623 B2 | 10/2013 | Poutiatine et al. |
| 8,552,868 B1 | 10/2013 | Ferguson |
| 8,574,189 B2 | 11/2013 | Poutiatine et al. |
| 8,600,548 B2 | 12/2013 | Bossi et al. |
| 8,636,172 B2 | 1/2014 | Dunn |
| 8,666,539 B2 | 3/2014 | Ervin |
| 8,666,543 B2 | 3/2014 | MacVittie et al. |
| 8,669,863 B2 | 3/2014 | Alhuwaishel |
| 8,670,865 B2 | 3/2014 | Coe |
| 8,725,291 B2 | 5/2014 | Czaja et al. |
| 8,727,180 B2 | 5/2014 | Zonana et al. |
| 8,734,061 B2 | 5/2014 | Terzini |
| 8,753,308 B2 | 6/2014 | Palmer et al. |
| 8,778,393 B2 | 7/2014 | Palmer et al. |
| 8,807,131 B1 | 8/2014 | Tunnell et al. |
| 8,821,454 B2 | 9/2014 | Kriesel et al. |
| 8,854,225 B2 | 10/2014 | Johnson |
| 8,874,260 B2 | 10/2014 | Saltsov |
| 8,905,964 B2 | 12/2014 | Poutiatine et al. |
| 8,922,367 B2 | 12/2014 | Denny et al. |
| 8,973,338 B2 | 3/2015 | Terzini |
| 8,976,036 B2 | 3/2015 | Johnson |
| 8,985,388 B2 | 3/2015 | Ratnakar |

(56) References Cited

U.S. PATENT DOCUMENTS

| | | | |
|---|---|---|---|
| 9,010,584 B2 | 4/2015 | Law et al. | |
| 9,014,847 B2 | 4/2015 | Dunn | |
| 9,019,097 B2 | 4/2015 | Choi et al. | |
| 9,037,291 B2 | 5/2015 | Terzini | |
| 9,043,015 B2 | 5/2015 | Ratnakar | |
| 9,066,847 B2 | 6/2015 | Poutiatine et al. | |
| 9,066,849 B2 | 6/2015 | Fung et al. | |
| 9,155,682 B2 | 10/2015 | Boyd | |
| 9,161,885 B1 | 10/2015 | Zhou | |
| 9,211,559 B2 | 12/2015 | Law et al. | |
| 9,218,458 B2 | 12/2015 | Baarman et al. | |
| 9,235,689 B2 | 1/2016 | Ervin | |
| 9,283,363 B1 | 3/2016 | Scorzelli et al. | |
| 9,289,583 B2 | 3/2016 | Palmer et al. | |
| 9,346,068 B2 | 5/2016 | Knight et al. | |
| 9,361,772 B2 | 6/2016 | Johnson | |
| 9,381,139 B2 | 7/2016 | Fung et al. | |
| 9,414,599 B2 | 8/2016 | Leonardi | |
| 9,418,207 B1 | 8/2016 | Patton et al. | |
| 9,436,298 B2 | 9/2016 | Draper et al. | |
| 9,439,835 B2 | 9/2016 | DiMartino et al. | |
| 9,566,402 B2 | 2/2017 | Djupesland | |
| 9,636,195 B2 | 5/2017 | Wolpo | |
| 9,731,103 B1 | 8/2017 | Rouse et al. | |
| 9,795,296 B2 | 10/2017 | Imran | |
| 9,839,500 B2 | 12/2017 | Flyash et al. | |
| 9,968,777 B1 | 5/2018 | Demarest et al. | |
| 2001/0009398 A1 | 7/2001 | Sekura et al. | |
| 2001/0022758 A1 | 9/2001 | Howard | |
| 2003/0174554 A1 | 9/2003 | Dunstone et al. | |
| 2004/0008123 A1 | 1/2004 | Carrender et al. | |
| 2004/0117062 A1 | 6/2004 | Bonney et al. | |
| 2004/0158194 A1 | 8/2004 | Wolff et al. | |
| 2004/0158349 A1 | 8/2004 | Bonney et al. | |
| 2005/0119604 A1* | 6/2005 | Bonney | A61M 15/0083 604/19 |
| 2005/0202363 A1 | 9/2005 | Osterwalder | |
| 2005/0226918 A1* | 10/2005 | MacDonald | A61K 9/0097 424/434 |
| 2005/0230409 A1 | 10/2005 | von Schuckmann | |
| 2006/0138162 A1 | 6/2006 | Anderson et al. | |
| 2006/0166157 A1 | 7/2006 | Rahman et al. | |
| 2006/0184271 A1 | 8/2006 | Loveless | |
| 2006/0213921 A1 | 9/2006 | Abdulhay et al. | |
| 2006/0218015 A1 | 9/2006 | Walker et al. | |
| 2006/0234189 A1 | 10/2006 | Duret | |
| 2006/0282010 A1 | 12/2006 | Martin et al. | |
| 2007/0075842 A1 | 4/2007 | Russell et al. | |
| 2007/0093932 A1 | 4/2007 | Abdulhay et al. | |
| 2007/0009856 A1 | 5/2007 | Ko | |
| 2007/0095851 A1 | 5/2007 | Anderson et al. | |
| 2007/0135790 A1 | 6/2007 | Auerbach | |
| 2007/0138195 A1 | 6/2007 | Anderson et al. | |
| 2007/0145065 A1 | 6/2007 | Anderson et al. | |
| 2007/0170199 A1 | 7/2007 | York | |
| 2007/0228065 A1 | 10/2007 | Anderson et al. | |
| 2007/0261985 A1 | 11/2007 | Allen | |
| 2007/0271001 A1 | 11/2007 | Ratnakar | |
| 2008/0008978 A1 | 1/2008 | Conrad et al. | |
| 2008/0017658 A1 | 1/2008 | Wright | |
| 2008/0027291 A1 | 1/2008 | Williams-Hartman | |
| 2008/0027579 A1 | 1/2008 | van der Hoop | |
| 2008/0054008 A1 | 3/2008 | Wright | |
| 2008/0059228 A1 | 3/2008 | Bossi et al. | |
| 2008/0060148 A1 | 3/2008 | Pinyayev | |
| 2008/0140250 A1 | 6/2008 | Dave | |
| 2008/0227046 A1 | 9/2008 | Lowe et al. | |
| 2008/0251530 A1 | 10/2008 | Holloway et al. | |
| 2008/0283542 A1 | 11/2008 | Lanka et al. | |
| 2008/0300719 A1* | 12/2008 | Duke | G07F 9/026 221/206 |
| 2009/0127157 A1 | 5/2009 | Costa et al. | |
| 2009/0208898 A1 | 8/2009 | Kaplan | |
| 2009/0210032 A1* | 8/2009 | Beiski | A61N 1/0548 264/16 |
| 2009/0223994 A1 | 9/2009 | Getz | |
| 2009/0272766 A1 | 11/2009 | Liable | |
| 2009/0277461 A1 | 11/2009 | Gallagher, Jr. et al. | |
| 2009/0277921 A1 | 11/2009 | Angelucci et al. | |
| 2010/0006589 A1 | 1/2010 | Klein | |
| 2010/0096399 A1 | 4/2010 | Ratnakar | |
| 2010/0100237 A1 | 4/2010 | Ratnakar | |
| 2010/0110725 A1 | 5/2010 | Chang | |
| 2010/0185456 A1 | 7/2010 | Kansal | |
| 2010/0318218 A1 | 12/2010 | Muncy, Jr. et al. | |
| 2010/0332023 A1 | 12/2010 | Tripathi et al. | |
| 2011/0011883 A1 | 1/2011 | Nakkouri | |
| 2011/0021983 A1 | 1/2011 | Jurson | |
| 2011/0027746 A1 | 2/2011 | McDonough et al. | |
| 2011/0060455 A1 | 3/2011 | Bogash et al. | |
| 2011/0060457 A1 | 3/2011 | De Vrught et al. | |
| 2011/0142554 A1 | 6/2011 | Terzini | |
| 2011/0146835 A1 | 6/2011 | Terzini | |
| 2011/0152757 A1 | 6/2011 | Beck et al. | |
| 2011/0160901 A1 | 6/2011 | Abrams, Jr. et al. | |
| 2011/0202174 A1 | 8/2011 | Bogash et al. | |
| 2011/0259910 A1 | 10/2011 | Knudsen | |
| 2011/0295416 A1 | 12/2011 | Aquilonius et al. | |
| 2011/0307592 A1 | 12/2011 | de la Huerga | |
| 2012/0055948 A1 | 3/2012 | Leifeld et al. | |
| 2012/0160716 A1 | 6/2012 | Chan et al. | |
| 2012/0165975 A1 | 6/2012 | Yi et al. | |
| 2012/0289905 A1 | 11/2012 | Julian et al. | |
| 2013/0025607 A1 | 1/2013 | Altounian | |
| 2013/0088328 A1 | 4/2013 | DiMartino et al. | |
| 2013/0116818 A1 | 5/2013 | Hamilton | |
| 2013/0120115 A1 | 5/2013 | Valls Chaparro et al. | |
| 2013/0165828 A1 | 6/2013 | Sullivan | |
| 2013/0168405 A1 | 7/2013 | Yuyama et al. | |
| 2013/0211270 A1 | 8/2013 | St. Laurent et al. | |
| 2013/0236851 A1 | 9/2013 | McDonough et al. | |
| 2013/0253286 A1 | 9/2013 | Fridman | |
| 2013/0256331 A1 | 10/2013 | Giraud et al. | |
| 2013/0280671 A1 | 10/2013 | Brawn et al. | |
| 2013/0304255 A1 | 11/2013 | Ratnakar | |
| 2013/0306191 A1 | 11/2013 | Metzmaker et al. | |
| 2013/0323673 A1 | 12/2013 | Hakomori et al. | |
| 2013/0345859 A1 | 12/2013 | Omura et al. | |
| 2014/0031975 A1 | 1/2014 | Poutiatine et al. | |
| 2014/0046676 A1 | 2/2014 | Kibler et al. | |
| 2014/0072932 A1 | 3/2014 | Brawn et al. | |
| 2014/0074283 A1 | 3/2014 | Blackburn | |
| 2014/0093836 A1 | 4/2014 | Wolpo | |
| 2014/0114472 A1 | 4/2014 | Bossi et al. | |
| 2014/0195043 A1 | 7/2014 | Ervin | |
| 2014/0203021 A1 | 7/2014 | Zill | |
| 2014/0207278 A1 | 7/2014 | Czaja et al. | |
| 2014/0227657 A1 | 8/2014 | Sanders | |
| 2014/0257051 A1 | 9/2014 | Cam et al. | |
| 2014/0263423 A1 | 9/2014 | Akdogan et al. | |
| 2014/0263425 A1 | 9/2014 | Akdogan et al. | |
| 2014/0267719 A1 | 9/2014 | Akdogan et al. | |
| 2014/0277705 A1 | 9/2014 | Czaja et al. | |
| 2014/0277707 A1 | 9/2014 | Akdogan et al. | |
| 2014/0277710 A1 | 9/2014 | Akdogan et al. | |
| 2014/0278508 A1 | 9/2014 | Akdogan et al. | |
| 2014/0278510 A1 | 9/2014 | McLean et al. | |
| 2014/0303989 A1 | 10/2014 | Ferguson | |
| 2014/0305963 A1 | 10/2014 | Zonana et al. | |
| 2014/0316799 A1 | 10/2014 | Cosgrove et al. | |
| 2014/0324216 A1 | 10/2014 | Beg et al. | |
| 2014/0326744 A1 | 11/2014 | Ratnakar | |
| 2014/0339248 A1 | 11/2014 | Reddy et al. | |
| 2014/0339249 A1 | 11/2014 | Reddy et al. | |
| 2014/0346184 A1 | 11/2014 | Bae et al. | |
| 2014/0346186 A1 | 11/2014 | Reddy et al. | |
| 2014/0350720 A1 | 11/2014 | Lehmann et al. | |
| 2014/0371904 A1 | 12/2014 | Parviainen | |
| 2015/0012131 A1 | 1/2015 | Saltsov | |
| 2015/0021349 A1 | 1/2015 | Sanders | |
| 2015/0038898 A1 | 2/2015 | Palmer et al. | |
| 2015/0044628 A1 | 2/2015 | Flyash | |
| 2015/0048101 A1 | 2/2015 | Reddy et al. | |
| 2015/0072300 A1 | 3/2015 | Wolpo | |

(56) References Cited

U.S. PATENT DOCUMENTS

| | | |
|---|---|---|
| 2015/0072306 A1 | 3/2015 | Barnard et al. |
| 2015/0076174 A1 | 3/2015 | Mersmann |
| 2015/0079533 A1 | 3/2015 | Lowe |
| 2015/0174348 A1 | 6/2015 | Tunnell et al. |
| 2015/0174349 A1 | 6/2015 | Tunnell et al. |
| 2015/0191268 A1 | 7/2015 | Paz |
| 2015/0191294 A1 | 7/2015 | Paz |
| 2015/0221086 A1 | 8/2015 | Bertram |
| 2015/0232256 A1 | 8/2015 | Hoover et al. |
| 2015/0257980 A1 | 9/2015 | Fung et al. |
| 2015/0259110 A1 | 9/2015 | Blackburn |
| 2015/0266654 A1 | 9/2015 | Baarman et al. |
| 2015/0272825 A1 | 10/2015 | Lim et al. |
| 2015/0273165 A1 | 10/2015 | Hadash |
| 2015/0291344 A1 | 10/2015 | Macvittie et al. |
| 2015/0305671 A1 | 10/2015 | Yoon et al. |
| 2015/0317455 A1 | 11/2015 | Lehmann et al. |
| 2015/0320643 A1 | 11/2015 | Zhou |
| 2015/0328084 A1 | 11/2015 | Cash |
| 2015/0342830 A1 | 12/2015 | Bujalski et al. |
| 2015/0347713 A1 | 12/2015 | Seeger |
| 2015/0359667 A1 | 12/2015 | Brue |
| 2016/0012249 A1 | 1/2016 | Keppler |
| 2016/0016720 A2 | 1/2016 | Paz |
| 2016/0022542 A1 | 1/2016 | Lehmann et al. |
| 2016/0029962 A1 | 2/2016 | Hyde et al. |
| 2016/0037916 A1 | 2/2016 | Hermann |
| 2016/0038377 A1 | 2/2016 | Tegborg et al. |
| 2016/0042150 A1 | 2/2016 | Moloughney |
| 2016/0066776 A1 | 3/2016 | Weiss et al. |
| 2016/0096014 A1 | 4/2016 | Ajiki et al. |
| 2016/0107820 A1 | 4/2016 | Macvittie et al. |
| 2016/0113747 A1 | 4/2016 | Almutairi |
| 2016/0117480 A1 | 4/2016 | Ervin |
| 2016/0128906 A1 | 5/2016 | Baarman et al. |
| 2016/0132660 A1 | 5/2016 | Barajas et al. |
| 2016/0136056 A1 | 5/2016 | Lapham |
| 2016/0145031 A1 | 5/2016 | Reinhold et al. |
| 2016/0158107 A1 | 6/2016 | Dvorak et al. |
| 2016/0166766 A1 | 6/2016 | Schuster et al. |
| 2016/0180693 A1 | 6/2016 | Johnson |
| 2016/0203292 A1 | 7/2016 | Kamen et al. |
| 2016/0211693 A1 | 7/2016 | Stevens et al. |
| 2016/0213606 A1 | 7/2016 | Palmer et al. |
| 2016/0213843 A1 | 7/2016 | Despa et al. |
| 2016/0228333 A1 | 8/2016 | Bukstein et al. |
| 2016/0278899 A1* | 9/2016 | Heller ................. A61K 31/198 |
| 2016/0338810 A1 | 11/2016 | Schmalhurst et al. |
| 2016/0366946 A1 | 12/2016 | Murison et al. |
| 2016/0367188 A1* | 12/2016 | Malik ................... G16H 40/67 |
| 2017/0007383 A1 | 1/2017 | Blank |
| 2017/0027675 A1 | 2/2017 | Nahshon |
| 2017/0028178 A1 | 2/2017 | Skoba |
| 2017/0197025 A1 | 7/2017 | Adams et al. |
| 2017/0265978 A1 | 9/2017 | Borotto et al. |
| 2017/0304854 A1 | 10/2017 | Jacquemart et al. |
| 2017/0312181 A1 | 11/2017 | Davis et al. |
| 2017/0333649 A1 | 11/2017 | Djupesland |
| 2018/0110939 A1 | 4/2018 | Lanzkowsky |
| 2018/0184795 A1 | 7/2018 | Pai et al. |
| 2018/0353388 A1 | 12/2018 | Rouse et al. |
| 2019/0091061 A1* | 3/2019 | Radmand ................ A61F 5/566 |

FOREIGN PATENT DOCUMENTS

| | | |
|---|---|---|
| CN | 203417402 | 2/2014 |
| CN | 105263552 | 1/2016 |
| CN | 105873631 | 8/2016 |
| DE | 102014114601 A1 | 4/2016 |
| KR | 101221415 B1 | 1/2013 |
| WO | WO2004062717 A1 | 7/2004 |
| WO | WO2010062675 A1 | 6/2010 |
| WO | WO2011151056 A1 | 12/2011 |
| WO | WO2013062785 A1 | 5/2013 |
| WO | WO2015150240 A1 | 10/2015 |
| WO | WO2015172962 A1 | 11/2015 |
| WO | WO2015181693 A1 | 12/2015 |
| WO | WO2015196293 A1 | 12/2015 |
| WO | WO2015196336 A1 | 12/2015 |
| WO | WO2016064592 A1 | 4/2016 |
| WO | WO2016064688 A1 | 4/2016 |
| WO | WO2016064786 A1 | 4/2016 |
| WO | WO2016064906 A1 | 4/2016 |
| WO | WO2016064908 A1 | 4/2016 |
| WO | WO2016116591 A1 | 7/2016 |
| WO | WO2017064709 A1 | 4/2017 |
| WO | WO2017218947 A1 | 12/2017 |
| WO | WO 2018/075979 A1 | 4/2018 |
| WO | WO 2018/075981 A2 | 4/2018 |
| WO | WO2019178367 A1 | 9/2019 |

OTHER PUBLICATIONS

International Search Report and Written Opinion, PCT/US2018/013440, dated Mar. 9, 2018, 11 pages.
International Search Report and Written Opinion, PCT/US2019/022287, dated Jul. 16, 2019, 13 pages.
International Search Report and Written Opinion, PCT/US2020/034044, dated Aug. 10, 2020, 22 pages.
European Patent Office, "European Search Report", for Application No. 18739166.9-1132, dated Oct. 1, 2020, 8 pages.
Chinese Office Action, Application No. 201880013266.6, dated Dec. 18, 2020, 7 pages.
Australian Office Action, Application No. 2019235911, dated Jan. 13, 2021, 6 pages.
Australian Patent Office, Examination Report, Application No. 2019235911, mailed Mar. 25, 2021, 3 pages.
Australian Patent Office, Examination Report, Application No. 2019235911, mailed Jul. 14, 2021, 5 pages.
Japanese Office Action, First Office Action, Application No. 2019-55890, Aug. 3, 2021, with Translation, 6 pages.
Japanese Patent Office, Japanese Office Action dated May 9, 2023 for Application No. 2022-125665, 2 pages.
New Zealand Patent Office, New Zealand Office Action dated May 4, 2023 for Application No. 755322, 3 pages.
Japanese Patent Office, Notice of Reasons for Rejection for Japanese patent application No. 2019-558990, Trial No. 2022-12257, Mailing No. 113478, dated Jan. 24, 2023, 2 pages (translation three pages).

* cited by examiner

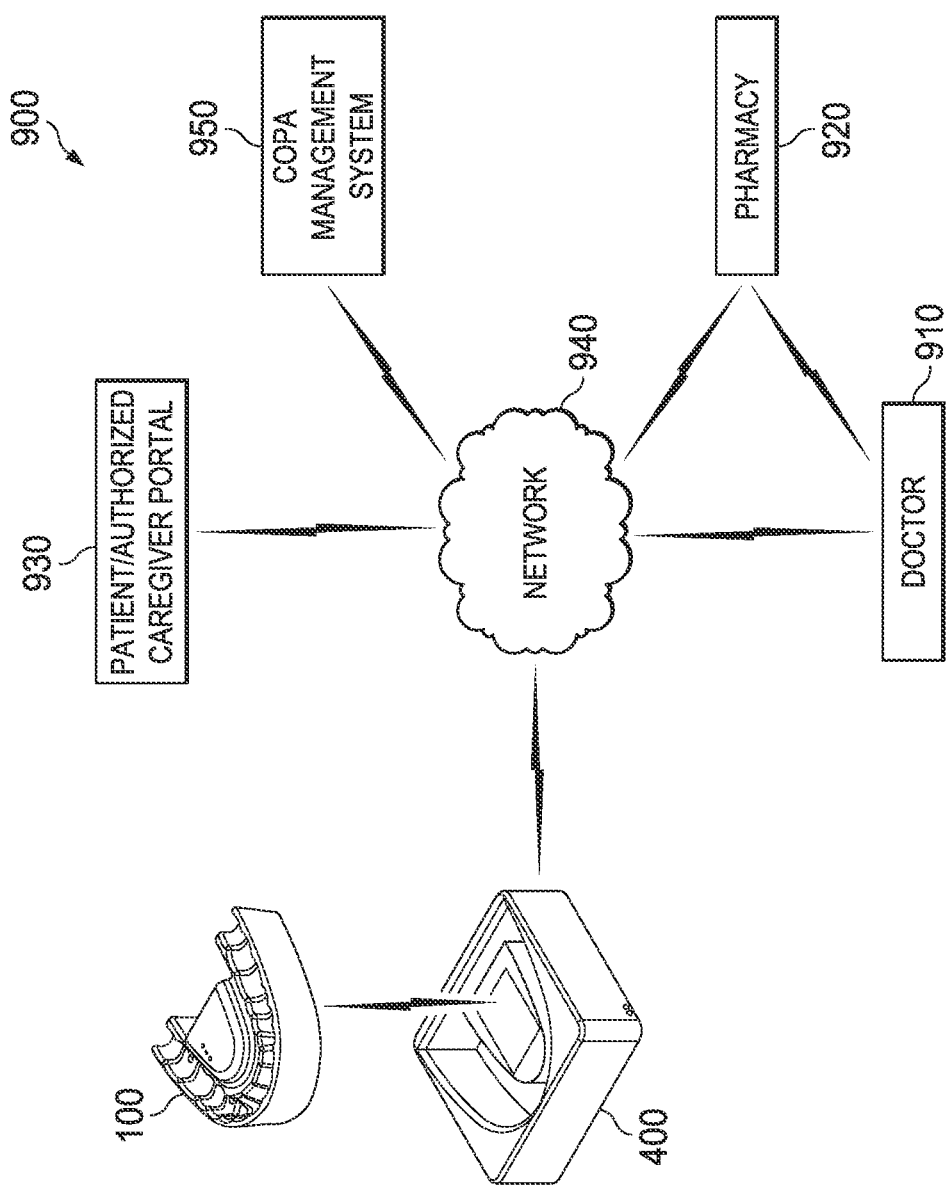

COMPUTERIZED ORAL PRESCRIPTION ADMINISTRATION DEVICES AND ASSOCIATED SYSTEMS AND METHODS

CROSS REFERENCE TO RELATED APPLICATIONS

The present application is a continuation application of U.S. patent application Ser. No. 16/246,122, filed Jan. 11, 2019, which is a continuation application of U.S. patent application Ser. No. 15/674,046, filed Aug. 10, 2017, now U.S. Pat. No. 10,188,840, which is a continuation application of U.S. patent application Ser. No. 15/406,043, filed Jan. 13, 2017, now U.S. Pat. No. 9,731,103, each of which is hereby incorporated by reference in its entirety.

The present application is related to U.S. patent application Ser. No. 15/708,045, filed Sep. 18, 2017, now U.S. Pat. No. 9,981,116, which is a continuation application of U.S. patent application Ser. No. 15/674,046, filed Aug. 10, 2017, now U.S. Pat. No. 10,188,840, which is a continuation application of U.S. patent application Ser. No. 15/406,043, filed Jan. 13, 2017, now U.S. Pat. No. 9,731,103, each of which is hereby incorporated by reference in its entirety.

TECHNICAL FIELD

The present disclosure relates generally to pharmaceutical oral dose administration devices, and more particularly, to computerized oral prescription administration (COPA) devices and associated systems and methods.

INTRODUCTION

The history of pharmacology has produced a continual evolution of routes of administration, pharmaceutical formulations, dosage forms, and dosing devices in a continuing quest towards maximizing the effective benefit and relative costs of prescription medications. Administration of prescribed substances may begin in controlled healthcare settings, for example, at a healthcare facility or by a physician at a patient's home. Early-stage formulations may include liquid forms for parenteral (e.g., into a blood stream) and enteral (e.g., into a gastro-intestine) administration including elixirs, tonics, solutions, suspensions, syrups and eventually injections, intravenous (IVs), and epidurals. The early-stage formulations may be developed to produce advanced forms, for example, via mechanization and formulation research. The early-stage formulations, the advanced forms, and further research and clinical studies such as patient acceptances of the early-stage formulations and/or the advanced forms may contribute to the routes of administration, pharmaceutical formulations, dosage forms, and dosing devices.

As the healthcare treatment transitioned from limited emergency involvement into longer term chronic illness care, higher percentages of the prescribed medication administration shifts from the controlled healthcare settings to patient managed settings. In a patient managed setting, outside the control of a trained healthcare staff, the administration of liquid formulations may be difficult due to non-specific dosing instructions. Dosing based on teaspoon and/or tablespoon measurements may be vague and variable. Dosing cups may have different measurement formats, and thus may cause confusion in a patient managed setting. In addition, dosing cups are often separated from initial prescription bottles, and thus may lead to erroneous administration.

The advancements of mechanical manufacturing systems and pharmacology research enabled patient managed administrations of prescribed substances to shift from liquid formulations to pills (e.g., tablets or capsule-formulations), which may have increased shelf life and allow for patient ease of use, dosing exactness, and production cost reductions. Thus, a majority of oral medications in patient managed settings are now pills. Additionally, there is an increased interest in microparticulate formulations including pellets, granules, micro particles, mini tablets, and the like. However, patients, such as infants, elderly, or impaired patients, that cannot or prefer not to swallow tablets or capsule-formulations may be given enteral oral liquid prescriptions through dosing syringes in patient managed settings. In addition, parenteral liquid formulations are still commonly administered in controlled healthcare settings since the parenteral liquid formulations often have the fastest rate of absorption and the most expedient success in the desired result and can improve localized administration, inventory control, fraud prevention, and administration path audit capability.

Depending on the entity managing the administration of a drug, various forms of the drug may be developed to meet expectations, needs, and challenges of different entities. While there are some exceptions based on effectiveness and toxicity, most pharmaceutical manufacturers may produce multiple formulations of drugs to support different routes of administration and dosing.

There is a growing demand for drug administration in patient controlled or managed settings as consumers increasingly engage in preventative or resultative treatment plans, which involve drug administration in patient controlled settings. For example, outpatient surgeries and/or one-day inpatient surgery stays are increasingly common for significant medical procedures, which may involve subsequent drug administrations at a patient's home. In addition, as the population ages, the demand for prescription management increases. Consumers may take multiple over-the-counter and/or prescribed medicines daily, where the medicines are commonly in the form of pills. Unfortunately, the ease-of-use of pills and the increasing number of consumers engaged in chronic patient managed treatment plans has led to misuse and mismanagement of many drug classes.

For example, pill forms are lightweight, portable, recipient non-specific, difficult for inventory management, don't carry individual identification number, have extensive shelf life, and are inexpensive to produce. Thus, the intakes or usages of pills are difficult to control once outside of healthcare managed environments. In addition, to achieve the economy of scale in the manufacturing process, pill production is scheduled based on maximizing the output of the machines, materials, and/or ingredients available instead of based on future demands. With a few exceptions, a minimal amount of the pills produced are wasted since pills remain active for a long time. Pills proliferate our society and have become conduits to addiction and abuse.

One such patient managed treatment that is highly susceptible to prescription misuse and mismanagement is opioid pain treatment. For example, according to the Food and Drug Administration (FDA), approximately 100 million people in the United States (US) suffer from pain in a given year. About 9 to 12 million of the pain sufferers have chronic or persistent pain, while the remaining pain sufferers have short-term pain from injuries, illnesses, or medical procedures. In 2014, the Centers for Disease Control and Prevention reported that the number of annual opioid prescriptions in the US is about equal to the number of adults in the US population. While pain sufferers should benefit from skillful and appropriate pain management, the misuse or addiction of opioids needs to be controlled. FDA leaders and physicians attempt to address the opioid epidemic by balancing two complementary principles: deal aggressively with opioid misuse and addiction while protecting the well-being of people experiencing acute or chronic pains. However, the pain sufferers in areas where reforms, policies, and restrictions aimed at opioid misuse have been implemented may not experience the balance. Some states have implemented additional known addict or misuser databases that must be checked by providers prior to prescribing. However, physicians may not check the databases prior to prescribing due to the burden of using the systems and/or they may not want to restrict access by true chronic pain sufferers. Other states have implemented reporting and audit trails to track physicians that have prescribed from the opioid family. However, to avoid the additional steps and potentials for audit scrutiny, some physicians may refuse to offer pain management or short-term pain prescriptions, and may refer all cases to pain clinics.

Attempts at improved patient education, enhanced labeling, restrictive prescribing, have led to higher costs for providers, patients, pharmacies, and insurance companies and less overall effectiveness for the patients. In the end, true pain suffers struggle to have access to opioids while opioid misusers continue to manipulate the available avenues for access regardless of the apparent oversights put in place. Policies and plans at various levels have not been successful and are not sufficient to control or reduce the misuse of prescription drugs. Accordingly, improved devices, systems, and methods for drug administration are needed.

SUMMARY

The following summarizes some aspects of the present disclosure to provide a basic understanding of the discussed technology. This summary is not an extensive overview of all contemplated features of the disclosure, and is intended neither to identify key or critical elements of all aspects of the disclosure nor to delineate the scope of any or all aspects of the disclosure. Its sole purpose is to present some concepts of one or more aspects of the disclosure in summary form as a prelude to the more detailed description that is presented later.

The present disclosure provides computerized oral prescription administration (COPA) devices and associated systems and methods. The COPA devices and associated systems and methods facilitate the controlled dispensing of medication to an intended user. In this regard, the identification of the intended user can be verified based on the dentition of the user before dispensing of the medication from the device. Further, the timing and/or volume of medication dispensed from the device can be controlled in accordance with dosage instructions for the intended user. Parameters associated with the dispensing of medication (e.g., medication, dosage amount, timing, intended user information, etc.) can be tracked, stored in a COPA management system, and/or communicated throughout the healthcare continuum, including medical personnel, pharmaceutical personnel, patient, authorized caregivers, and/or insurers, such that patient's compliance with a treatment plan can be evaluated and/or the effectiveness of the treatment plan can be evaluated. Additionally, the COPA management system can send out alerts to participants of the healthcare continuum to serve as notices, reminders, and/or issues.

In one embodiment, a substance dispensing apparatus is provided. The apparatus includes a mouthpiece having a recess sized and shaped to mate with an intended user's dentition; a sensing element coupled to the mouthpiece and configured to determine whether the intended user's dentition is positioned within the recess; and an actuator coupled to the mouthpiece and in communication with the sensing element, the actuator configured to dispense a substance from a reservoir coupled to the mouthpiece in response to the sensing element determining that the intended user's dentition is positioned within the recess.

In some embodiments, the sensing element is configured to determine whether the intended user's dentition is positioned within the recess by comparing position data of a user's dentition positioned within the recess to predetermined position data associated with the intended user's dentition. In some embodiments, the sensing element includes a position sensor embedded within the mouthpiece. In some embodiments, the sensing element includes a plurality of positions sensors spaced embedded within the mouthpiece along the recess. In some embodiments, the sensing element is configured to determine whether the intended user's dentition is positioned within the recess by comparing pressure data of a user's dentition positioned within the recess to predetermined pressure data associated with the intended user's dentition. In some embodiments, the sensing element includes at least one pressure sensing element embedded within the mouthpiece. In some embodiments, the pressure sensing element is configured to monitor pressure at a plurality of locations along the recess. In some embodiments, the recess is sized and shaped to mate with at least one of a lower row of teeth or an upper row of teeth of the intended user.

In some embodiments, the apparatus further comprises a processor in communication with the sensing element and the actuator. In some embodiments, the apparatus further comprises memory in communication with the processor. In some embodiments, the memory includes dosage instructions for the substance for the intended user. In some embodiments, the dosage instructions include at least a dosage amount and a dosage timing for dispensing the substance to the intended user. In some embodiments, the processor is configured to send an instruction to the actuator to dispense the substance from the reservoir in accordance with the dosage instructions in response to the sensing element determining that the intended user's dentition is positioned within the recess. In some embodiments, the processor is configured to initiate alerts based on the dosage instructions. In some embodiments, the processor is configured to initiate the alerts by communicating with a communication device of the intended user. In some embodiments, the processor is configured to initiate the alerts based on a dosage timing of the dosage instructions. In some embodiments, the processor is configured to initiate the alerts by communicating with a communication device of a medical provider. In some embodiments, the processor is configured to initiate the alerts based on a failure to dispense the substance in accordance with the dosage instructions. In some embodiments, the processor is configured to store dispensing data associated with the substance being dispensed from the reservoir in the memory. In some embodiments, the dispensing data includes a dispensed amount and/or a dispensed time.

In some embodiments, the substance includes a liquid. In some embodiments, the actuator includes a pump. In some embodiments, the reservoir includes a plurality of compartments, each of the plurality of compartments configured to contain a substance for dispensing to the intended user. In some embodiments, the actuator is configured to dispense the substance from each of the plurality of compartments. In some embodiments, the actuator includes a single actuator configured to dispense the substance from each of the plurality of compartments. In some embodiments, the actuator includes a plurality of actuators, where each actuator is configured to dispense the substance from a corresponding compartment.

In one embodiment, a method of dispensing a substance to an intended user is provided. The method includes determining whether an intended user's dentition is positioned within a recess of a mouthpiece, the recess sized and shaped to mate with the intended user's dentition; and dispensing a substance from a reservoir coupled to the mouthpiece in response to determining that the intended user's dentition is positioned within the recess of the mouthpiece.

In some embodiments, position data or pressure data is compared to corresponding predetermined position or pressure data to determine whether the intended user's dentition is positioned within the recess includes. In some embodiments, the substance is dispensed in accordance with dosage instructions for the intended user. In some embodiments, the method further comprises storing dispensing data associated with the substance being dispensed from the reservoir. The dispensing data can include a dispensed amount and/or a dispensed time.

Additional aspects, features, and advantages of the present disclosure will become apparent from the following detailed description.

BRIEF DESCRIPTION OF THE DRAWINGS

Illustrative embodiments of the present disclosure will be described with reference to the accompanying drawings, of which:

FIG. 9 is a schematic diagram of a COPA system according to embodiments of the present disclosure.

DETAILED DESCRIPTION

Figure 1:
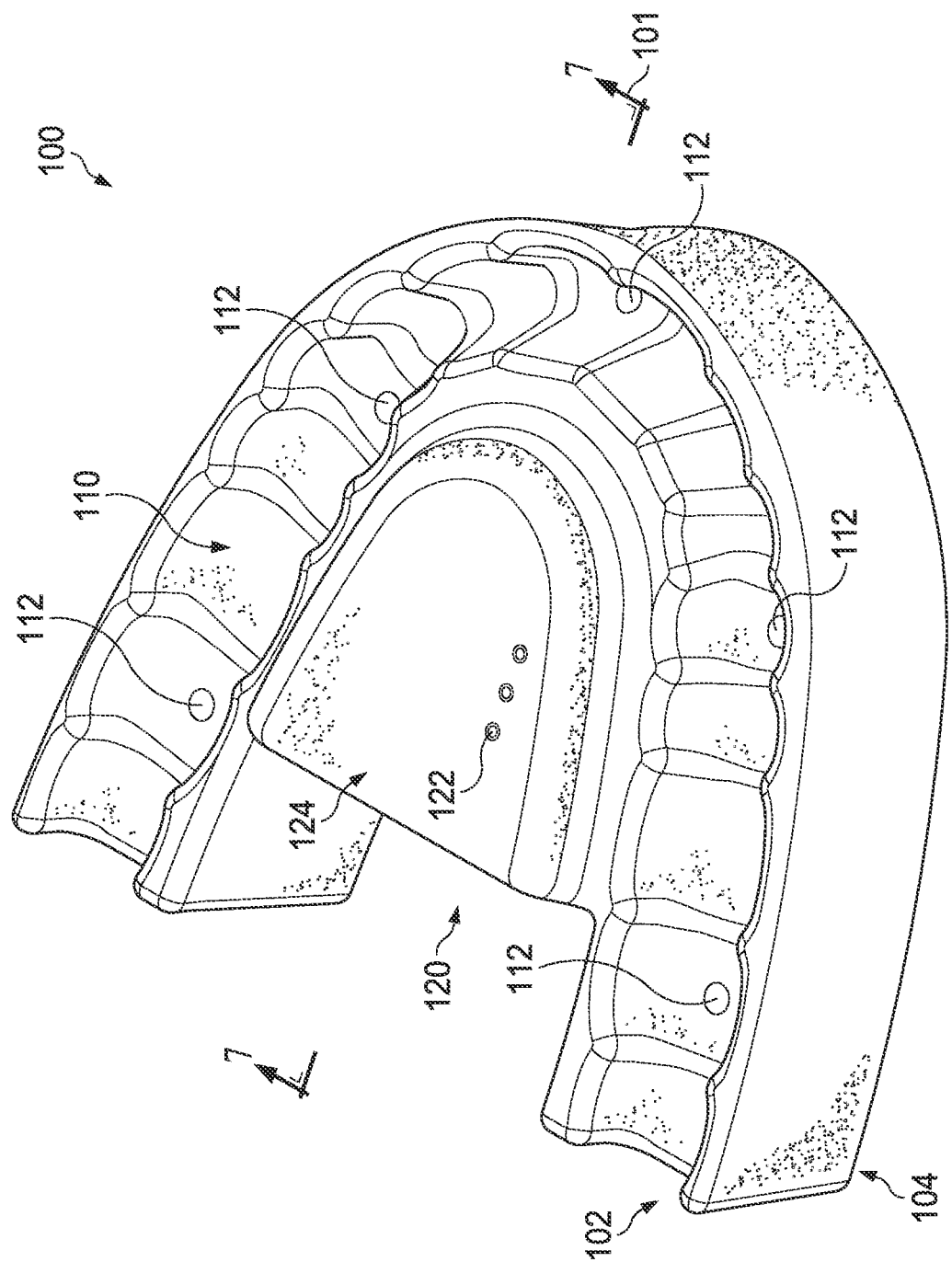
FIG. 1 is a top perspective view of a computerized oral prescription administration (COPA) device according to embodiments of the present disclosure.

For the purposes of promoting an understanding of the principles of the present disclosure, reference will now be made to the embodiments illustrated in the drawings, and specific language will be used to describe the same. It is nevertheless understood that no limitation to the scope of the disclosure is intended. Any alterations and further modifications to the described devices, systems, and methods, and any further application of the principles of the present disclosure are fully contemplated and included within the present disclosure as would normally occur to one skilled in the art to which the disclosure relates.

Embodiments of the present disclosure provide mechanisms for administering enteral oral medications through an ID-specific device registered with a centralized management system. In an embodiment, the device comprises a mouthpiece including a recess sized and shaped to mate with an intended user's dentition. The mouthpiece may include position and/or pressure sensors positioned at various locations within the recess. The mouthpiece may include a micro-pump unit including a processor, a reservoir, an actuator, flow channels, and exit valves. The reservoir may be filled with prescribed or over-the-counter medications. The processor may be in communication with the position and/or pressure sensors and the actuator. To administer the medications, the patient may insert the mouthpiece into the patient's mouth and close the mouth to bite on the mouthpiece. The position and/or pressure sensors may sense and measure the position of the user's dentition and associated pressures from the bite. The processor may determine whether a match is found between the measured positions and/or pressures and pre-recorded data of the intended recipient patient. The processor may determine whether the mouthpiece is positioned correctly. Upon detecting a match and correct positioning, the processor may activate the actuator to release an exact dosage of the medications through the flow channels and exit valves into the patient's mouth for ingestion. In an embodiment, the centralized management system may track the creation and preparation of the mouthpiece, the filling of the prescribed medications, and/or the administration or dispensing of the prescribed medications through various identification mechanisms.

The disclosed embodiments may provide several benefits. For example, the employment of the unique individual mouthpiece with the embedded processor and the centralized management system can ensure that the prescribed medications are delivered to the intended recipient. Thus, the disclosed embodiments may avoid misuse and mismanagement of prescription medications. In addition, the disclosed embodiments may allow healthcare providers and insurance companies to better track the administering of the prescribed medications and evaluate the benefits, effects, and/or results of the prescribed medications more accurately. The disclosed embodiments may deliver a precise dosage of prescribed medications to patients and may especially benefit patients that are elderly, impaired, or have behavioral issues that may limit their abilities to self-administer prescribed medications. While the disclosed embodiments are described in the context of using dentition as a form of verification for matching a prescription to an intended user, other biological markings (fingerprint, retina or iris scans, DNA, voice recognition, etc.) may also be applied or used in conjunction with and/or in lieu of the dentition matching.

FIG. 1 is a top perspective view of a COPA device 100 according to embodiments of the present disclosure. The COPA device 100 may be used for delivering enteral oral liquid, multiparticulate, and/or other forms of drugs to an intended patient or user with controlled dosing. The COPA device 100 is a mouthpiece including a top side 102 and an opposite bottom side 104. The top side 102 includes a recess 110. The recess 110 is sized and shaped to conform to an intended user's dentition. For example, the recess 110 includes an arrangement for receiving the intended user's upper teeth. The COPA device 100 may be constructed from a biocompatible impression material or polymer.

The recess 110 includes a plurality of sensors 112 positioned at various locations within the recess 110. In some embodiments, the sensors 112 may be pressure sensors or optical position sensors. For example, the sensors 112 may be embedded at locations in contact with crevices, nooks, and gum lines of the user. When the user closes his or her mouth around the COPA device 100 using normal or force bite, the sensors 112 can determine whether the user's dentition is positioned within the recess 110. In some embodiments, the sensors 112 may be housed on one or more agile or flexible filament strands embedded within the recess 110. For example, each filament strand may be coupled between two and twenty sensors 112 or any suitable number of sensors 112. In some embodiments, the sensors 112 may be formed and distributed on a meshed structure embedded within the recess 110. The meshed structure may include any suitable number of sensors 112. The sensors 112 on the meshed structure or the filament strand may allow a pressure profile to be created when the user closes his or her mouth on the COPA device 100. In an embodiment, the sensors 112 may monitor and take position and/or pressure measurements when the user closes his or her mouth. The position and/or pressure measurements may be compared to pre-determined data of the user's dentition as a form of verification to identify an intended recipient of a prescribed substance, as described in greater detail herein.

The COPA device 100 further includes a sealed prescription dispensing unit 120. The sealed prescription dispensing unit 120 may be positioned at the top center of the COPA device 100. The sealed prescription dispensing unit 120 may include a sealed sleeve 124 and a plurality of access ports 122 extending from a top side of the sealed sleeve 124 into the prescription dispensing unit 120. The access ports 122 may be configured to receive prescribed substances. For example, a clinician or pharmacy technician may fill prescribed substances into the prescription dispensing unit 120 via the access ports. The prescribed substances may include formulations in various forms, such as liquid and/or multi-particulate. The prescription dispensing unit 120 may include other components, such as a processor, chambers, flow channels, actuators (e.g., micro-pumps), and exit valves, as described in greater detail herein.

The COPA device 100 may provide patient identification functionalities via the patient's teeth imprint in the recess 110. For example, each individual has a unique dental imprint. While there are certain patterns for the ages at which certain teeth may erupt, mature, and be replaced with permanent teeth and for alignment of teeth types, the setting, size, angle, distance between certain points within a patient's mouth, and the resulting bite are different for different patients. In addition, damaged teeth, missing teeth, filled teeth, capped teeth, and prosthetics such as crowns, bridges, partial, and full dentures further the identifying nature or uniqueness of the mouths of different individuals. Thus, the use of the COPA device 100 with the dentition imprint can be effective in identifying a particular individual. The COPA device 100 may provide further patient identification functionalities via various patient verification mechanisms implemented by a processor coupled to the mouthpiece (e.g., embedded within the sealed prescription dispensing unit 120), as described in greater detail herein.

The COPA device 100 further provides controlled prescription administration functionalities via the sealed prescription dispensing unit 120. For example, the processor may be in communication with the sensors 112 and configured to determine whether the COPA device 100 is correctly positioned within the intended user's mouth. Upon detecting a correct position, the processor may control the components within the sealed prescription dispensing unit 120 to release or deliver an exact dosage of the prescribed substances into the intended user's mouth, as described in greater detail herein.

Figure 2:
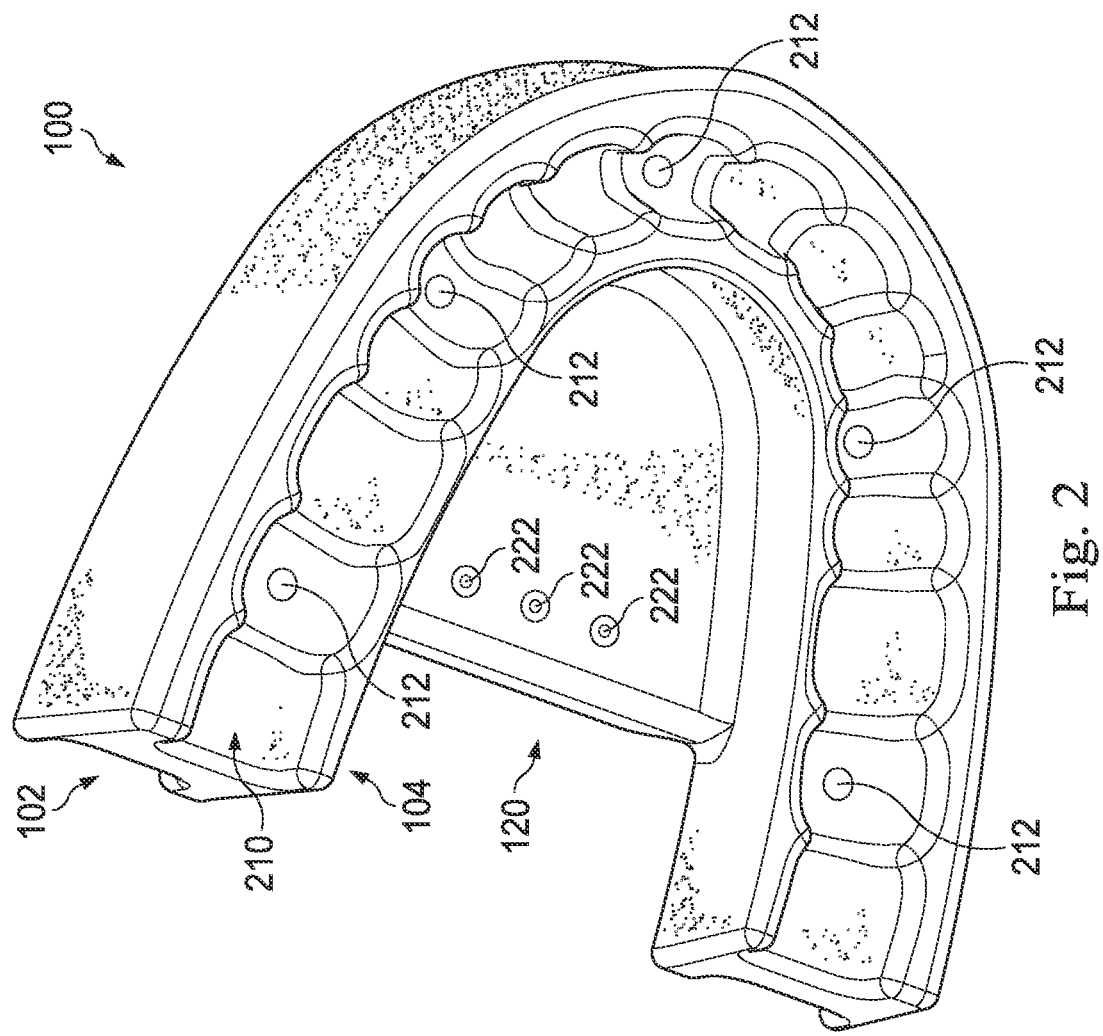
FIG. 2 is a bottom perspective view of a COPA device according to embodiments of the present disclosure.

FIG. 2 is a bottom perspective view of the COPA device 100 according to embodiments of the present disclosure. The bottom side 104 includes a recess 210 sized and shaped to conform to an intended user's dentition, for example, the lower teeth. The recess 210 is embedded with a plurality of sensors 212 similar to the sensors 112. The sensors 212 may be coupled to flexible or agile filament strands or a meshed structure. The prescription dispensing unit 120 includes a plurality of exit valves 222 on the bottom side 104, where prescribed substances may be released. While the COPA device 100 is illustrated with a top recess 110 imprinted with an intended user's upper teeth and a bottom recess 210 imprinted with an intended user's lower teeth, the COPA device 100 can include a single recess 110 or a single recess 210 to provide substantially similar functionalities.

Figure 3:
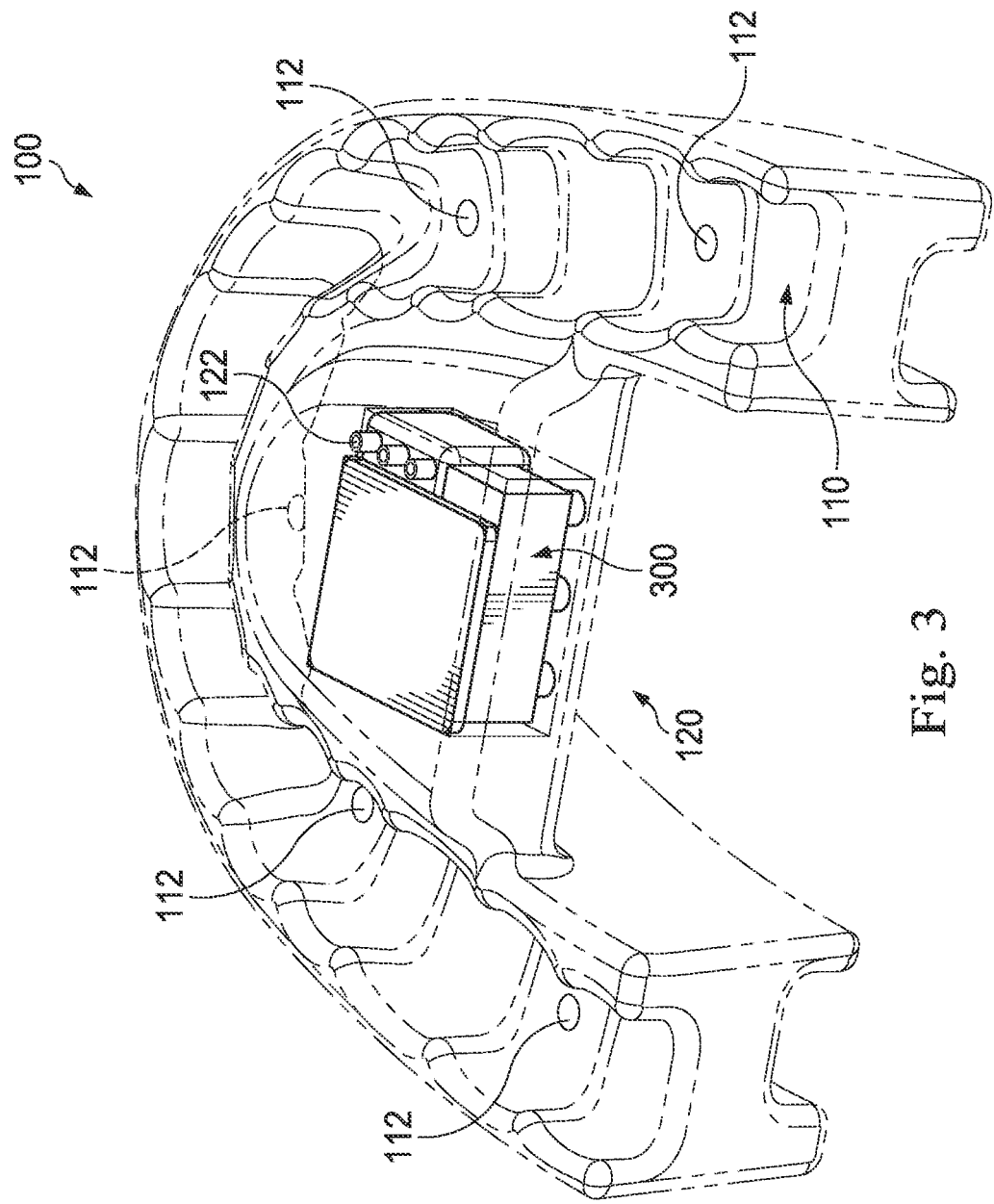
FIG. 3 is a perspective view of a COPA device according to embodiments of the present disclosure.

FIG. 3 is a perspective view of the COPA device 100 according to embodiments of the present disclosure. FIG. 3 illustrates the COPA device 100 with an upper portion of the sealed sleeve 124 (shown in FIG. 1) removed to provide a more detailed view of the prescription dispensing unit 120. As shown, the prescription dispensing unit 120 includes a micro-pump unit 300. The access ports 122 may be in communication with the micro-pump unit 300 to allow prescribed substances to be filled into the micro-pump unit 300.

Figure 4:
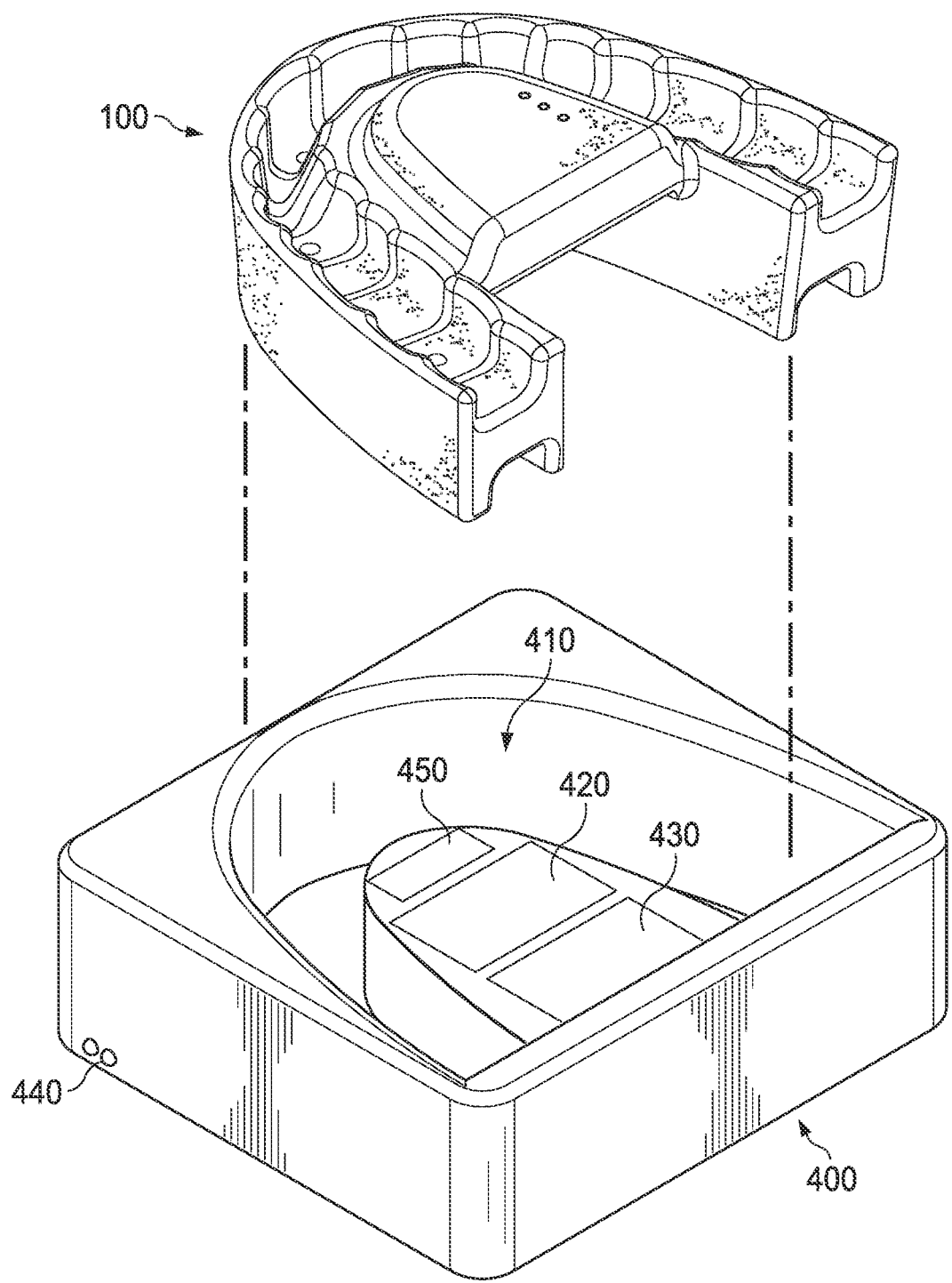
FIG. 4 is a perspective view of a COPA device positioned for docking at a docking station according to embodiments of the present disclosure.
Figure 5:
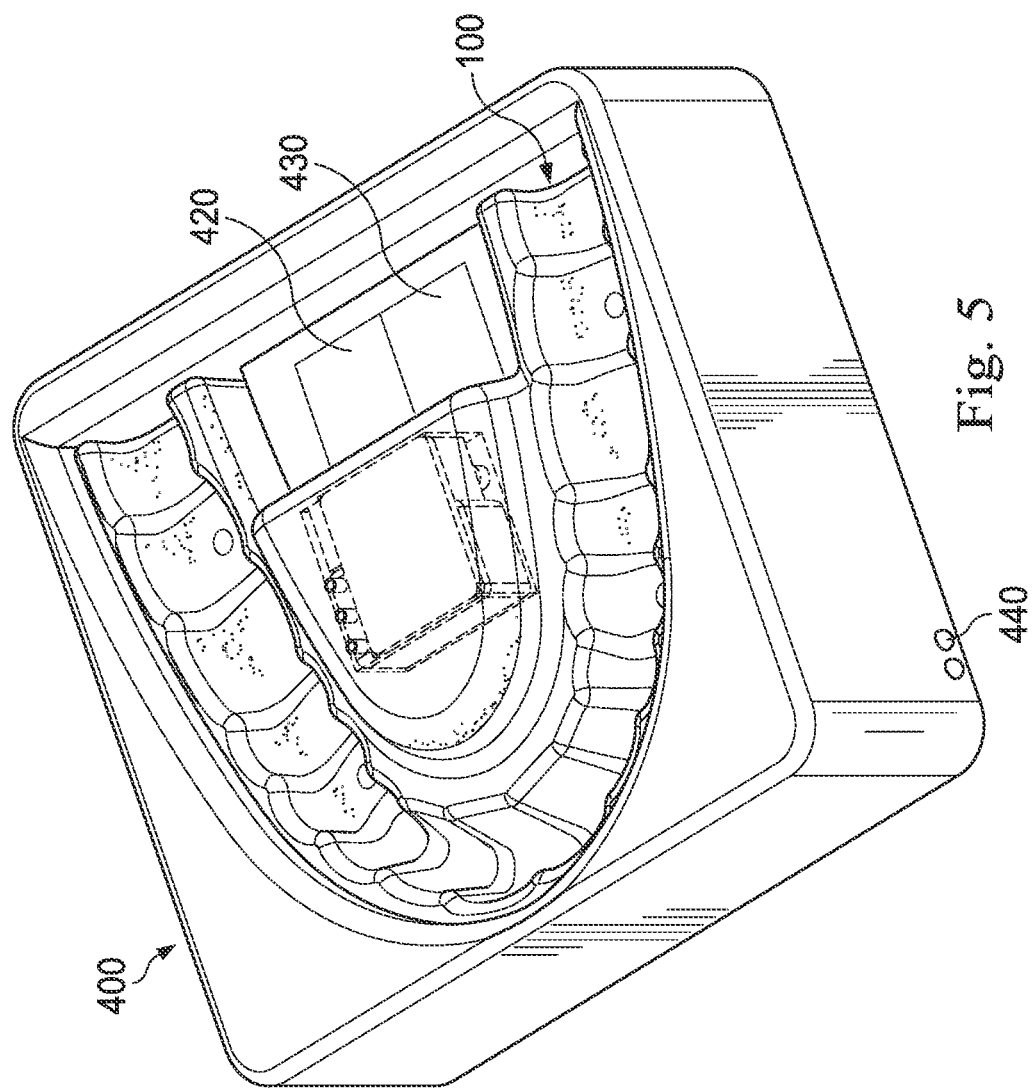
FIG. 5 is a perspective view of a COPA device docked at a docking station according to embodiments of the present disclosure.

FIG. 4 is a perspective view of the COPA device 100 positioned for docking at a docking station 400 according to embodiments of the present disclosure. FIG. 5 is a perspective view of the COPA device 100 docked at the docking station 400 according to embodiments of the present disclosure. The COPA device 100 may be positioned into the docking station 400 for storage, charging, and/or communicating over a communications network. The docking station 400 may include a docking compartment 410, a wireless transceiver 420, a charging component 430, a plurality of indicators 440, and a COPA device sensing component 450. The wireless transceiver 420, the charging component 430, the indicators 440, and the sensing component 450 may be arranged as shown or in any suitable configuration on the docking station 400.

The docking compartment 410 may be sized and shaped to house the COPA device 100. The wireless transceiver 420 may be configured to transmit and receive data while the COPA device 100 is docked at the docking station 400 via a patient private wireless network, as described in greater detail herein. The charging component 430 may include a haptic charging component (e.g., for charging batteries) and may be configured to charge the COPA device 100 while the COPA device 100 is docked at the docking station 400. For example, the operations of the processor, the actuators, and the releasing of the prescribed substances operate based on electrical power. The COPA device sensing component 450 may be configured to detect whether the COPA device 100 is docked correctly. For example, the bottom side 104 of the COPA device 100 may further include a docking station sensing component, where alignment between the COPA device 100 and the docking station 400 may be detected via the COPA device sensing component 450 and the docking station sensing component. After detecting alignment, the charging component 430 may begin to charge the COPA device 100. In addition, the COPA device 100 may upload prescription administration activities via the wireless transceiver 420 to a COPA management system, as described in greater detail herein. The indicators 440 may include light-emitting diodes (LEDs). The indicators 440 may be configured to indicate whether the COPA device 100 is positioned correctly within the docking compartment 410 for charging and wireless communications. The indicators 440 may be further configured to indicate the charging status (e.g., power on/off) of the COPA device 100 and/or the wireless transmission and/or reception activities of the wireless transceiver 420.

In some embodiments, the docking station 400 provides a closed loop control system that can sense and detect the present of the COPA device 100 at various stages of use and/or storage and provide corresponding feedback and/or alerts to the user, caregiver, doctor, and/or pharmacy. For example, the indicators 440 may be configured to indicate that the COPA device 100 is within proximity of the docking station 400, properly docked within the docking station 400, improperly docked within the docking station 400, charging, fully charged, transferring data, operating properly, operating improperly, and/or other status indications. In some embodiments, the docking station 400 may include a sound generation component (e.g., a speaker) that can generate various tones and/or vibrations to indicate a current status, including the proximity or docking of the COPA device 100, charging activities, and/or communication activities. In some embodiments, the docking station 400 can be in communication with a computing device such as a smartphone, tablet, or computer (e.g., via a wireless transceiver 420 or via a wired connection) and may send the feedback and/or alerts (as well as logs of prescription administration activities obtained from the COPA device 100) to a COPA smartphone or tablet application.

The COPA device 100 may be placed in the docking station 400 between dosages for storage, charging and/or communication as needed (e.g., multiple times per day, daily, nightly, weekly, etc.). The charging and/or power needs of the COPA device 100, including the prescription dispensing unit 120, may be minimal since the operations associated with dispensing the medications may typically span short durations (e.g., 1 minute or less). In addition to charging and wireless communications, the docking station 400 may help prevent the COPA device 100 from being lost, misplaced, or damaged. For example, the docking station 400 may further include locking mechanisms to provide additional protocols for matching the COPA device 100 to an intended user. In an embodiment, the docking station 400 may include a thumbprint or optical scanning component configured to unlock or release the COPA device 100 based on a thumbprint verification against the intended user's thumbprint or any other biological markings.

To prevent a successful matching and unlocking of the COPA device 100 by an unintended user for subsequent release of the prescription, the processor within the prescription dispensing unit 120 may be further configured to limit the activation time for the release of the prescription in conjunctions with the locking mechanisms. For example, a charged COPA device 100 may be inserted into a patient's mouth for drug delivering or releasing at a designated time. When the administering of the medication is not time-specific, the controlling of the medication release time may begin after an initial use. For example, the processor may be configured to record the time of the initial use and control subsequent releases based on an elapsed time duration or an interval between prescribed dosages. The processor may be configured to release the drug at a designated time or designated time durations for subsequent deliveries.

Figure 6:
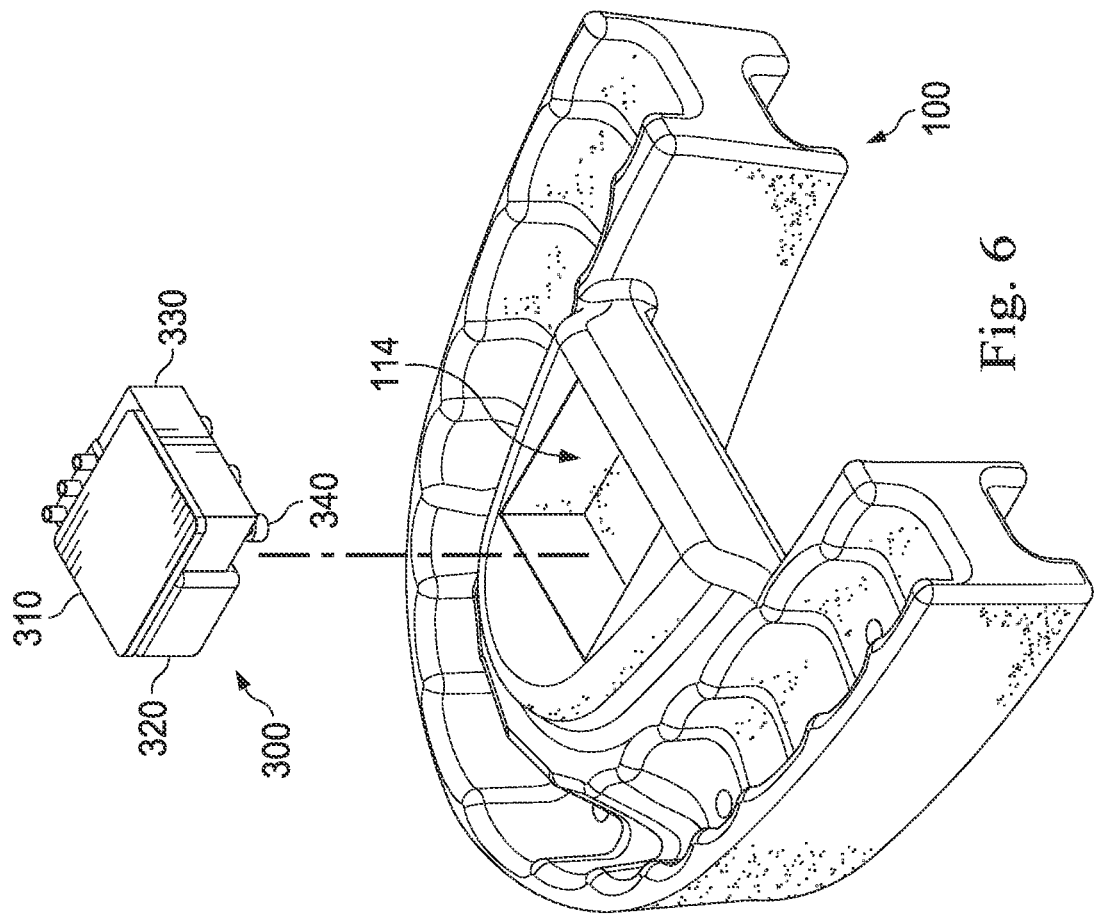
FIG. 6 is a perspective view of a COPA device and a pre-packaged micro-pump unit positioned for coupling according to embodiments of the present disclosure.
Figure 7:
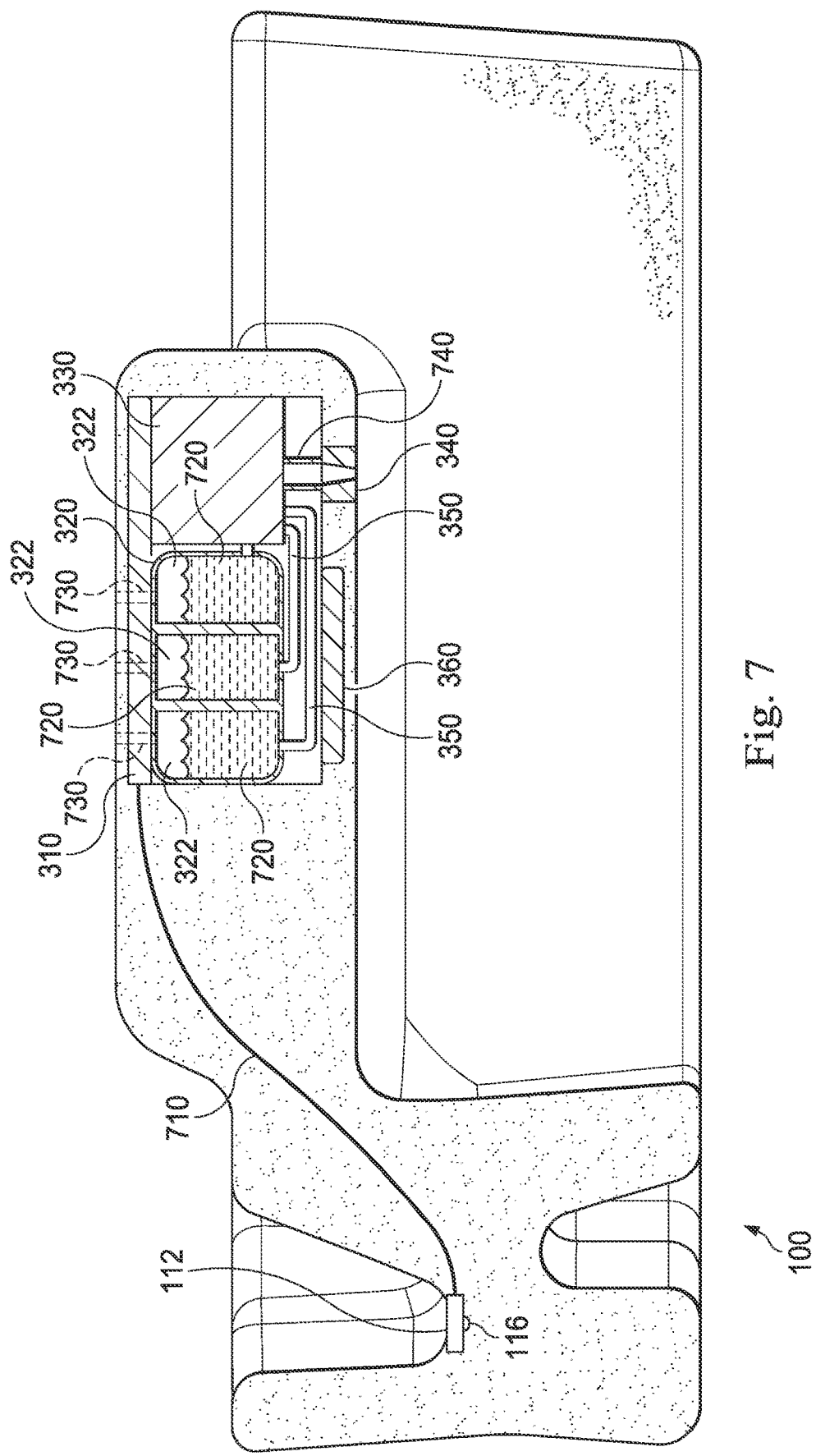
FIG. 7 is a cross-sectional view of a COPA device according to embodiments of the present disclosure.
Figure 8:
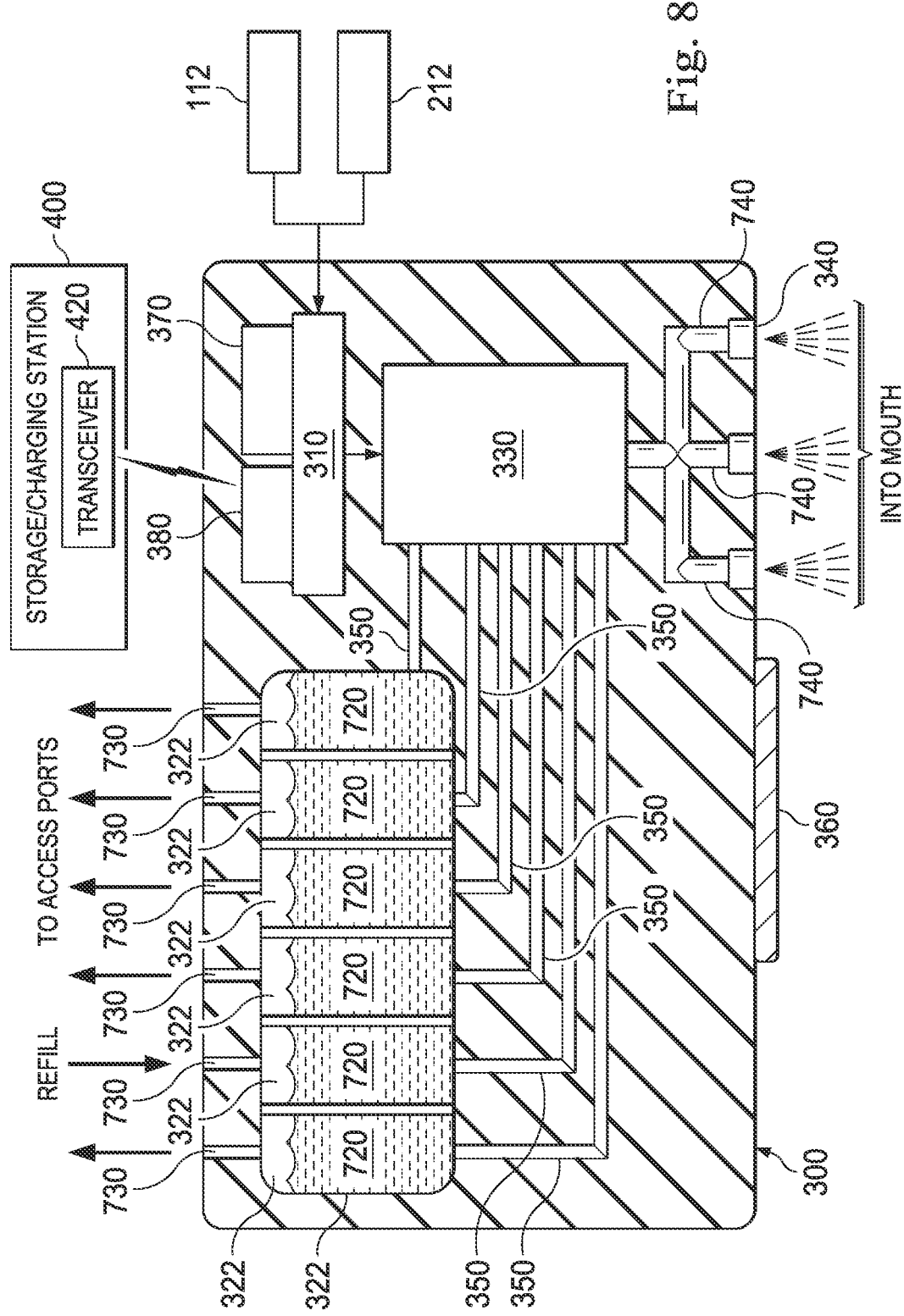
FIG. 8 is a schematic diagram of a micro-pump unit according to embodiments of the present disclosure.

FIG. 6 is a perspective view of the COPA device 100 and the micro-pump unit 300 positioned for coupling according to embodiments of the present disclosure. The micro-pump unit 300 is the core of the prescription dispensing unit 120. The micro-pump unit 300 includes a processor 310, a reservoir 320, an actuator 330, and a plurality of exit valves 340. The processor 310 is configured to control the micro-pump unit 300 and record activities associated with the COPA device 100, for example, dosage delivery time and amount, charged time, and/or wireless communication activities. The reservoir 320 is configured to hold a prescribed substance, for example, as formulated for delivery via the micro-pump unit 300. The actuator 330 is configured to push or deliver an exact dosage of the prescribed substance upon activation. The exit valves 340 are positioned at the bottom of the micro-pump unit 300 and are configured to release the prescribed substance for ingestion. More detailed views of the micro-pump unit 300 are shown in FIGS. 7 and 8 and the interactions among the components of the micro-pump unit 300 are described in greater detail below. The micro-pump unit 300 may be pre-packaged with a prescription through various mechanisms, as described in greater detail herein. As shown, the COPA device 100 may include a compartment 114 sized and shaped to receive the micro-pump unit 300. For example, the pre-packaged micro-pump unit 300 may be positioned within the compartment 114 and covered by the sealed sleeve 124 (shown in FIG. 1) to form the sealed prescription dispensing unit 120.

FIG. 7 provides a detailed view of the internal components of the micro-pump unit 300 and the interactions among the internal components according to embodiments of the present disclosure. In this regard, FIG. 7 is a cross-sectional view of the COPA device 100 according to embodiments of the present disclosure. The cross-sectional view is taken along the line 101 of FIG. 1. While FIG. 7 is illustrated with one of the sensors 112 positioned on a flexible or agile filament 116, the sensor 112 may be positioned on a meshed structure as described above. The micro-pump unit 300 is positioned within the compartment 114 (shown in FIG. 4) of the COPA device 100. The micro-pump unit 300 may further include a charging component 360 (e.g., batteries) and a memory 370 (shown in FIG. 8). The charging component 360 may be in communication with the processor 310 and the actuator 330. When the COPA device 100 is docked at the docking station 400 as shown in FIG. 4, the charging component 360 may be coupled to the charging component 430 of the docking station 400 and configured to charge the COPA device 100 (e.g., the processor 310 and the actuator 330) via battery charging or wireless charging. The memory 370 may include volatile memory and non-volatile memory of any suitable memory types, including random access memory (RAM), read-only memory (ROM), programmable read-only memory (PROM), erasable programmable read-only memory (EPROM), electrically erasable programmable read-only memory (EEPROM), dynamic random-access memory (DRAM), static random-access memory (SRAM), and combinations thereof.

The processor 310 can be in communication with the sensor 112, for example, via a wire 710, and the actuator 330. The actuator 330 can be in communication with the reservoir 320 and the exit valves 340 via flow channels 350. The reservoir 320 can be in communication with the access ports 122 (shown in FIG. 1) and the flow channels 350.

The reservoir 320 may include one or more chambers 322, for example, one, two, three, four, five, six, or any suitable number of chambers 322. The chambers 322 may be configured to hold a prescribed substance 720. In this regard, the number and size of the chambers 322 can be selected based on the number of prescribed substances, type(s) of prescribed substances, and/or dosage amounts to be used. The chambers 322 can be any size that will still allow the device to be positioned within the mouth of a patient. In some instances, the chambers 322 are in communication with corresponding chambers or channels formed in the COPA device 100 to allow an increased volume of storage for the prescribed substance(s). The chambers 322 may be in communication with the access ports 122. In some embodiments, each chamber 322 is in communication with one of the access ports 122 through access cannulas 730.

A clinician or a pharmacy technician may fill or refill the prescribed substance 720 via the access ports 122. The prescribed substance 720 may include liquid formulations, powder formulations, multiparticulate formulations, or any other suitable formulations. In some embodiments, all chambers 322 are filled with liquid formulations. In some other embodiments, one chamber 322 may be filled with a liquid formulation and another chamber 322 may be filled with a powder or multiparticulate formulation. The prescribed substance 720 in the different chambers 322 may be released at the same time to form a particular formulation or at different times to prevent certain active ingredients in the prescribed substances 720 from reacting with each other. In this regard, each chamber 322 may contain a different prescribed substance 720 for the intended user.

The actuator 330 may be a micro-pump suitable for delivery of pharmaceutical formulations. The actuator 330 may be activated or triggered by the processor 310 to cause the prescribed substances 720 to flow through the flow channels 350 and exit cannulas 740 and release via the exit valves 340. The actuator 330 may be activated one or more times to release an exact dosage of the prescribed substances 720. The flow channels 350 may be constructed from suitable tubing materials. The exit valves 340 may be any suitable flow control valves, for example, with elastomeric membranes, configured to prevent leakage of the prescribed substances 720 into the user's mouth or backflow of the prescribed substance from the user's mouth into the COPA device 100.

The processor 310 may be any suitable microcontroller or microprocessor configured to perform the functions described herein, including functions such as performing patient identification and verification, performing position sensing and/or pressure detection (e.g., in conjunction with the sensors 112), instructing the actuator 330 to release a dose of the prescribed substance 720, controlling the opening of the exit valves 340, controlling operation of components of the micro-pump unit 300 in accordance with dosage instructions for an intended user, storing dispensing data, etc. The dosage instructions may include at least a dosage amount and timing for dispensing the substance to the intended user. The dosage instructions may be stored in the memory 370.

In operation, the COPA device 100 may be inserted into the mouth of a user. The user may close his or her mouth around the COPA device 100 and bite into the COPA device 100, which may trigger the sensors 112 to perform position and/or pressure measurements. The processor 310 may determine whether the COPA device 100 is correctly positioned within the user's mouth based on the measurements from the sensors 112. In some embodiments, position and/or pressure data of the user's mouth may be recorded and stored in the memory 370 when the COPA device 100 is created. The processor 310 may compare the current position and/or pressure measurements to the original position and/or pressure data to determine whether there is a match between the current user of the COPA device 100 and the intended user of the COPA device 100. The processor 310 may also compare the current position and/or pressure measurements to the original position and/or pressure data to determine whether the COPA device 100 is correctly positioned within the intended user's mouth.

When the user is verified as the intended user and the COPA device 100 is correctly positioned within the intended user's mouth, the processor 310 may send an activation instruction to the actuator 330 and open the exit valves 340 to administer one or more of the prescribed substances 720 stored in the micro-pump unit 300 in accordance with dosage instructions for the intended user. The activation of the actuator 330 and the opening of the exit valves 340 may be based on dosage instructions or prescriptions stored in the memory 370 when the prescribed substance 720 is filled.

In some embodiments, the COPA device 100 may include one or more indicators that can provide feedback and/or alerts to the user when the COPA device 100 is in use. The indicator(s) may include a vibrating component, a sound generation component (e.g., speaker), and/or a visual indicator component. For example, the vibrating component can cause the COPA device 100 to vibrate with different pulsing patterns to indicate the different statuses of the COPA device (e.g., one vibration to indicate proper user authentication and initiation of dispensing, two vibrations to indicate completion of dispensing, patterned or repeated vibrations to indicate an error with the COPA device, etc.). Similarly, the sound generation component can generate various tones and/or patterns to indicate the different statuses of the COPA device. Likewise, the visual indicator component can include one or more LEDs that display different colors and/or patterns to indicate the different statuses of the COPA device. The current status of the COPA device 100 may be determined based on feedback from the processor 310, the sensors 112 or 212 (e.g., correct or incorrect positioning of the COPA device 100), sensors for monitoring the dispensing of the substance (e.g., volume and/or flow sensors), the docking station 400, and/or other sensors or monitoring devices associated with the COPA device 100 and/or the docking station 400 for determining the status of the COPA device 100.

FIG. 8 is a schematic diagram of the micro-pump unit 300 according to embodiments of the present disclosure. FIG. 8 provides a more detailed view of the micro-pump unit 300 and interactions with the sensors 112 and the docking station 400. As shown, the micro-pump unit 300 may further include a wireless transceiver 380. The wireless transceiver 380 may implement any suitable wireless communication protocols. The wireless transceiver 380 may wirelessly communicate with the docking station 400, for example, to upload recorded activities or to download revised or new dosage instructions, as described in greater detail herein. Further, the wireless transceiver 380 may wirelessly communicate with other wireless communication devices, including a communication device (e.g., computer, tablet, smartphone, etc.) of the intended user. In this regard, the processor of the micro-pump unit 300 can be configured to initiate alerts or reminders to the user (e.g., based on a dosage timing of the dosage instructions) by triggering the intended user's communication device to issue such an alert or reminder (e.g., by activating an audible and/or visual indicator). Similarly, the processor of the micro-pump unit 300 and/or the docking station 400 can be configured to initiate alerts or reminders through communications with a communication device of a medical provider. For example, the micro-pump unit 300 and/or the docking station may alert the medical provider based on a failure to dispense the substance in accordance with the dosage instructions (e.g., the patient is not taking the medication as prescribed) and/or multiple failed attempts to authenticate the intended user (e.g., indicating that someone other than the intended user is attempting to access the medication or that the intended user is having difficulties using the device).

FIG. 9 is a schematic diagram of a system 900 according to embodiments of the present disclosure. The system 900 includes the COPA device 100, the docking station 400, a doctor 910, a pharmacy 920, a patient/authorized caregiver portal 930, and a central management system 950 in communication with each other via a network 940. The network 940 may include one or more wireless access networks and/or one or more wireline networks that may connect to a backbone network or the Internet. The network 940 may include network encryption and security policies for protecting patients' privacy. The network 940 may include cloud storage for data storage and retrieval across the network 940 based on the encryption and security policies. The doctor 910 may be a registered doctor for the prescription management system. The pharmacy 920 may be an approved pharmacy and/or a COPA device (e.g., the mouthpiece) fabricator. A COPA fabricator may be individuals or organizations trained in procuring standardized dental impressions (e.g., the COPA device 100) that capture varying individual elements of the intended recipients' dentition. The system 900 may provide an identification system for tracking the path of prescription administration and management to prevent misuse and mismanagement.

At a high level, the doctor 910 may prescribe a medication to a patient and the pharmacy 920 may create the mouthpiece for the patient and fill the mouthpiece according to the prescription(s) provided by the doctor 910. The pharmacy 920 may program the micro-pump unit of the mouthpiece to deliver an exact dosage of the prescribed medication and/or a dosage intake time. In this regard, dosage instructions for the patient may be stored in memory of the micro-pump unit. The patient may insert the mouthpiece into the patient's mouth and the micro-pump unit will, upon verification that the user is the intended recipient, dispense the prescribed medication as programmed. The patient may dock the mouthpiece at the docking station when the mouthpiece is not in use. The docking station may charge the mouthpiece and/or communicate with the doctor 910 and/or the pharmacy 920 via wireless and/or wired connections. The doctor 910 and/or the pharmacy 920 may monitor and retrieve information associated with the dispensing of the prescribed medication from the docking station 400. The doctor 910 may provide instructions to adjust the dosage instructions based on the monitoring and/or the retrieval information, and/or based on evaluations of the patient's progress. The pharmacy 920 may send instructions to the docking station 400 to adjust the dosage instructions stored in the memory of the micro-pump unit based on the order from the doctor 910. For example, when the mouthpiece is docked at the docking station, the dosage instructions stored in the memory can be updated or re-programmed accordingly. Alternatively, the dosage instructions stored in the memory can be updated or re-programmed at the pharmacy 920. Similarly, the doctor 910 may prescribe new medication based on the monitoring and/or the retrieval information, and/or based on evaluations of the patient's progress. The pharmacy 920 may refill the micro-pump unit 300 accordingly.

The patient/authorized caregiver portal 930 may be stored on a computer server or in cloud storage on the network 940. The management system 950 may be hosted on the network 940. The management system 950 may include a master database that stores information associated with the patient and all COPA activities. For example, the management system 950 may allow doctors (e.g., the doctor 910), assembly or fulfillment technicians, pharmacists (e.g., the pharmacy 920), and any healthcare personnel that partake in the COPA process to access at least some portions of the master database, for example, based on logins. In an embodiment, different personnel may have different login profiles and the accesses to the master database may be based on login profiles. In some embodiments, the patient/authorized caregiver portal 930 may be hosted on the management system 950 and may have certain accesses to the master database. The patient information may include an identification of the patient, health history, prescription history, identification of the processor 310 within the COPA device 100, identification of the docking station 400 at which the COPA device 100 is charged, etc. The patient's identification may include a social security number (SSN) of the patient or other unique identifier. The prescription history may include identifications of doctors (e.g., the doctor 910) who prescribed medications to the patient, identifications of pharmacies (e.g., the pharmacy 920) at which the prescribed medications were filled or refilled, identifications of the prescribed medications, and an identification of the processor 310 within the micro-pump unit 300 where the medications were filled. The prescription history may also be stored and managed by the management system 950. The physicians' identifications may include national provider identifiers (NPIs) of the physicians. The NPIS are unique identification number for Health Insurance Portability and Accountability Act (HIPPA) covered physicians. The pharmacies' identifications may include an impression technician identifier (ID), an assembly technician ID, and a registered pharmacy ID. The impression technician ID identifies the technician who created the COPA device 100 for the patient. The assembly technician ID identifies the technician who assembled or filled the prescribed medication into the micro-pump unit 300 of the COPA device 100. The pharmacy ID identifies the pharmacy at which the prescribed medication was filled. The prescribed medications' identifications may include dosage IDs that identify each prescribed substance or formulation filled into the micro-pump unit 300 of the COPA device 100.

In an embodiment, the doctor 910 may examine a patient and determine whether alternative therapies may be helpful to the patient. When the doctor 910 determines that the patient is in need of a particular medication, for example, according to guidelines for drug formulations based on COPA dosing options, the doctor may order a prescription for the patient. The doctor 910 may electronically transmit the prescription to the pharmacy 920 via the network 940, for example, according to HIPPA standards of protection for data and electronic medical record (EMR) formats.

At a COPA fabricator, an impression technician may take an impression of the intended patient's mouth and teeth to create a mold for the COPA device 100, for example, according to COPA guidelines and instructions. The mold may include a sealed sleeve similar to the sealed sleeve 124. For example, the impression technician may use a dental tray filled with bio friendly polymers to create an imprint of the patient's dentition. COPA approved dentists, hygienists, and/or other trained professions (e.g., a COPA device assembly technician) may complete the creation of the mold for the COPA device 100.

An assembly technician may prepare a pre-packaged micro-pump unit 300. Each micro-pump unit 300 may be identified based on an ID of the processor 310 embedded within the micro-pump unit. The assembly technician may record the ID of the micro-pump unit 300 in the management system 950. For example, the assembly technician may enter the ID into the management system 950, query a COPA device ID database of the management system 950 that stores and tracks IDs of COPA devices (e.g., the COPA device 100), and create a new record for the COPA device 100 created for the patient. The assembly technician may activate the processor 310 within the micro-pump unit 300, for example, wirelessly. The activation may include programming the processor 310 according to the order received from the doctor 910. The programming may include the dosage instructions for the patient (e.g., a dosage amount and the dosage timing for each prescribed medication). As described above, different chambers 322 may be filled with different formulations. Thus, the programming may include a release sequence, specific release times, and/or release durations for the different formulations, and/or intervals between releases. For example, some formulations may be programmed for instant release (IR) and some formulations may be programmed for extended release (ER).

After activating the micro-pump unit 300 or the processor 310, the assembly technician may place the activated micro-pump unit 300 into the top center of the mold where the sealed sleeve is positioned. The micro-pump unit 300 may be positioned such that the access cannulas 730 extend outside the sealed sleeve through the access ports 122 and the exit cannulas 740 extend through the base of the mold. The assembly technician may place a filament or a mesh of sensors 112 into the recess 110 of the COPA device 100. The assembly technician may attach a hose from an air compressor to the access ports 122 on top of the mold such that pressurized air may be pumped through the access cannulas 730 into the micro-pump unit 300 to ensure that the flow channels 350 are not compressed during the filling of the mold. The assembly technician may pump a liquid polymer into the mold and allow the liquid polymer to set. After the liquid polymer is set, the COPA device 100 is complete.

Upon completion of the COPA device 100, the COPA device 100 can be transferred to the pharmacy 920. At the pharmacy 920, a pharmacy staff (e.g., a COPA fulfillment technician) may place the COPA device 100 on a pedestal or other structure configured to allow access to the micro-pump unit 300 for filling. The pedestal may be covered by a sterile sleeve each time prior to placing a COPA device on the pedestal. The pharmacy staff may retrieve a record of the COPA device 100 based on the ID of the processor 310 within the COPA device 100, for example, from the COPA management system 950 via the network 940. The pharmacy staff may procure the medications (e.g., vials, pouches, bottles, etc.) from a drug manufacturer based on the dosage specified in the order received from the doctor 910. The pharmacy staff may update the record for the COPA device 100. The pharmacy staff may activate or open control valves at the access ports 122 to inject or deposit the formulated prescription (e.g., the prescribed substance 720) into one or more chambers 322 of the reservoir 320 via the access ports 122. After completing the filling, the pharmacy staff may close the control valves. The pharmacy staff may repeat the same process for filling other chambers 322 in the reservoir 320. Subsequently, the releasing of the formulated prescription is based on matching of the intended recipient's teeth and the COPA device 100 as described above. It should be noted that in some embodiments, the pharmacy 920 and the COPA fabricator may be the same entity.

The initial ID (e.g., of the processor 310) created for the COPA device 100 can be a permanent ID for the COPA device 100. Information associated with the filled prescription may be associated with the ID of the COPA device 100 and recorded in the management system 950 and/or an internal tracking system of the pharmacy 920. Thus, the COPA device 100 is fully traceable through the creation and preparation path. In addition, the mold used to craft the COPA device 100 may be assigned with a mold ID and may be stored in the management system 950 in association with the ID of the processor 310. Protocols for the use of the stored molds may be documented and records of subsequent mouthpieces may be stored in association in the management system 950. As such, misuse or fraud may be traced via the management system 950.

The pharmacy staff may pair the COPA device 100 with the docking station 400. The pharmacy staff may record an ID of the docking station 400 in association with the COPA device 100 in the management system 950. The wireless transceiver 420 of the docking station 400 may be recorded and registered in the management system 950 for remote access to the processor 310 embedded in the COPA device 100. For example, a pharmacy staff may adjust the dosage of the filled prescribed medication based on the instructions or an order of the prescribing doctor 910 by accessing the processor 310 via the wireless transceiver 420 without the patient returning the mouthpiece to the pharmacy 920 prior to depletion of the active ingredient(s). The adjustment may allow for a limited number of revisions, for example, to the dosing amount per release, the timing of the release, suspension of one or more of the chambers 322.

The patient may pick up the COPA device 100 and the docking station 400 from the pharmacy 920 and the pharmacy staff may provide instructions of usage to the patient. The patient may insert the COPA device 100 into the patient's mouth and close the mouth to bite on the COPA device 100 so that the prescription dispensing unit 120 or the micro-pump unit 300 may release the prescribed medication for ingestion. The patient may clean the COPA device 100 and dock the COPA device 100 at the docking station 400 after use.

The patient and/or the authorized care giver may have access to an online COPA account, for example, hosted on the management system 950 via the network 940. The wireless transceiver 420 may detect and transmit data such as activities recorded by the mouthpiece (e.g., dispensing dosages and timings for each medication) to the management system 950. The patient may view records of medications loaded into each chamber 322 of the COPA device 100. The patient may view records of the administration path of medications filled in the COPA device 100 including the initial prescription and any subsequent revisions. The patient may view records of anticipated depletion timeline for the patient to pick up a second pre-filled COPA device (e.g., the COPA device 100) and drop off the depleted COPA device if the treatment is a recurring treatment.

In an embodiment, the refill process for the COPA device 100 may use similar policies as today's drug refill policies. The COPA device 100 may be used in prolonged treatment plans. A prescribing doctor 910 may adjust and revise the prescription based on the treatment results observed from the patient. The doctor 910 may electronically transfer the revised prescription to the pharmacy 920. The pharmacy staff or the fulfillment technician may send revised instructions to the processor 310 wirelessly through the wireless transceiver 420 of the docking station 400. The management system 950 may house a full record of all revisions. When the intended recipient has depleted the COPA as planned, or as revised, the COPA device 100 may be returned to the pharmacy 920 for refills, for example, as directed by the prescribing doctor 910. The pharmacy staff may flush saline solution into the COPA device 100 through the access ports 122 into the sealed prescription dispensing unit 120 and out the exit valves 222. After flushing the COPA device 100, the pharmacy staff may refill the COPA device 100 based on the order received from the doctor 910 and may update the record in the management system 950. For example, if a prescription is written for three refills, the record would indicate three dosage IDs in association with the ID of the processor 310 of the COPA device 100 and previous dosage IDs. By recording all information associated with the COPA device 100, the patient and the dosage information in the management system 950 may be retrieved at any time, including when the patient changes providers or pharmacies during a treatment plan.

In an embodiment, when the COPA device 100 is no longer needed, for example, at the end of a treatment plan or change of treatment plan, the COPA device 100 may be deactivated and the management system 950 may be updated to indicate the deactivation of the COPA device 100. In some embodiments, when deactivation time of the COPA device 100 is within certain time limit, for example, X number of months, an assembly technician may reuse the original impression to build a new COPA device 100. The ID of the processor 310 within the new COPA device 100 may be stored in the management system 950 in association with the old ID of the old COPA device 100. In an embodiment, when a COPA device 100 needs to be recast due to actual change in the dentition of a recipient, the creation and preparation processes described above may be repeated. Information associated with the new mold may be stored on the management system 950 in association with the patient and the prescribed medications. By tracking all COPA devices 100 associated with a particular patient or a particular prescription, it may be less likely for an unintended user to gain access to the prescribed medications or for an intended user to provide false information for misuse of prescribed substance.

The following table lists reference numerals and corresponding reference names:

TABLE 1

Reference Numerals and Corresponding Reference Names.

| Reference Numerals | Reference Names |
| --- | --- |
| 100 | COPA device |
| 102 | top side |
| 104 | bottom side |
| 110 | recess |
| 112 | sensors |
| 114 | compartment |
| 116 | filament |
| 120 | prescription dispensing unit |
| 122 | access ports |
| 124 | sleeve |
| 210 | recess |
| 212 | sensors |
| 222 | exit valves |
| 300 | micro-pump unit |
| 310 | processor |
| 320 | reservoir |

TABLE 1-continued

Reference Numerals and Corresponding Reference Names.

| Reference Numerals | Reference Names |
| --- | --- |
| 322 | chambers |
| 330 | actuator |
| 340 | exit valves |
| 350 | flow channels |
| 360 | component |
| 370 | memory |
| 380 | wireless transceiver |
| 400 | docking station |
| 410 | docking compartment |
| 420 | wireless transceiver |
| 430 | component |
| 440 | indicators |
| 450 | COPA device sensing component |
| 710 | wire |
| 720 | prescribed substance |
| 730 | access cannulas |
| 740 | exit cannulas |
| 900 | system |
| 910 | doctor |
| 920 | pharmacy |
| 930 | patient/authorized caregiver portal |
| 940 | network |
| 950 | COPA management system |

Persons skilled in the art will recognize that the apparatus, systems, and methods described above can be modified in various ways. Accordingly, persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

What is claimed is:

1. A method of managing substance administration, the method comprising:
   receiving, by a substance management system, a dosage instruction for administering a substance to an intended user through a mouthpiece including a recess sized and shaped to receive a unique dentition of the intended user;
   receiving, by a sensing element positioned within the mouthpiece, data associated with a dentition of a user positioned within the recess;
   determining, by a processor positioned within a housing physically coupled to the mouthpiece, whether the unique dentition of the intended user is positioned within the recess of the mouthpiece based on a comparison between data associated with the unique dentition of the intended user being positioned within the recess and the data received from the sensing element dentition of a user positioned within the recess;
   receiving, by the substance management system, activity information associated with administering the substance to the intended user; and
   generating, by the substance management system, a record based on the received activity information.

2. The method of claim 1, wherein the dosage instruction includes at least one of a dosage amount or a dosage timing, and wherein the activity information includes at least one of an administered dosage amount or an administered dosage timing.

3. The method of claim 1, further comprising receiving, by the substance management system, identification information identifying the mouthpiece.

4. The method of claim 1, further comprising associating, by the substance management system, the record with at least one of an identifier of the intended user, identification information associated with the mouthpiece, the dosage instruction, or the activity information.

5. The method of claim 1, further comprising storing the record in a network storage.

6. The method of claim 5, further comprising:
receiving, by the substance management system, a request for the record; and
retrieving, by the substance management system, the record from the network storage in response to the request based on at least a security policy.

7. The method of claim 1, further comprising sending, by the substance management system, an alert to at least one of a communication device of the intended user or a communication device of a medical provider based on a failure to dispense the substance in accordance with the dosage instruction.

8. The method of claim 1, further comprising sending, by the substance management system, an alert to at least one of a communication device of the intended user or a communication device of a medical provider based on a dosage timing of the dosing instruction.

9. The method of claim 1, further comprising:
receiving, by the substance management system, a dosage update instruction for administering the substance; and
sending, by the substance management system, a substance dispense adjustment to the mouthpiece based on the dosage update instruction.

10. The method of claim 1, wherein the activity information is received from a wireless communication link in communication with the mouthpiece.

11. The method of claim 1, further comprising receiving, by the substance management system, identification information identifying the intended user.

12. The method of claim 1, wherein the sensing element includes at least one pressure sensing element embedded within the mouthpiece.

13. The method of claim 1, further comprising:
receiving, by the substance management system, a substance dispensing progress update based on the activity information; and
sending, by the substance management system, a substance dispense adjustment to the mouthpiece based on the substance dispensing progress update.

14. The method of claim 13, wherein receiving the substance dispensing progress update comprises receiving, by a docking station of the substance management system, the substance dispensing progress update, wherein the docking station is communicatively coupled to the mouthpiece.

15. The method of claim 14, wherein sending the substance dispense adjustment comprises sending, by the docking station, the substance dispense adjustment to the mouthpiece.

16. The method of claim 14, further comprising receiving, by the substance management system, identification information identifying the docking station.

17. The method of claim 1, wherein the record includes a prescription history of the intended user.

18. The method of claim 17, wherein the prescription history includes at least identification information for one or more dispensed substances that have been previously dispensed to the intended user.

19. The method of claim 17, wherein the prescription history includes at least identification information for one or more dispensing facilities that have previously provided the substance to the intended user.

* * * * *

UNITED STATES PATENT AND TRADEMARK OFFICE
CERTIFICATE OF CORRECTION

PATENT NO. : 12,076,517 B2
APPLICATION NO. : 17/379262
DATED : September 3, 2024
INVENTOR(S) : Thomas M. Rouse, Susan B. Owen and Christy Corey Page 1 of 1

It is certified that error appears in the above-identified patent and that said Letters Patent is hereby corrected as shown below:

In the Claims

At Claim 1, Column 18, Line 60, delete "dentition of a user positioned within the recess"

Signed and Sealed this
Seventeenth Day of June, 2025

Coke Morgan Stewart
*Acting Director of the United States Patent and Trademark Office*